(12) United States Patent
Chavez et al.

(10) Patent No.: US 10,584,328 B2
(45) Date of Patent: Mar. 10, 2020

(54) MUTANT VIRAL CAPSID LIBRARIES AND RELATED SYSTEMS AND METHODS

(71) Applicant: Adverum Biotechnologies, Inc., Menlo Park, CA (US)

(72) Inventors: Christopher Chavez, Santa Cruz, CA (US); Mehdi Gasmi, San Francisco, CA (US); Annahita Keravala, Palo Alto, CA (US); Thomas W. Chalberg, Redwood City, CA (US)

(73) Assignee: Adverum Biotechnologies, Inc., Menlo Park, CA (US)

( * ) Notice: Subject to any disclaimer, the term of this patent is extended or adjusted under 35 U.S.C. 154(b) by 250 days.

(21) Appl. No.: 15/388,380

(22) Filed: Dec. 22, 2016

(65) Prior Publication Data

US 2017/0183647 A1 Jun. 29, 2017

Related U.S. Application Data

(60) Provisional application No. 62/387,177, filed on Dec. 23, 2015.

(51) Int. Cl.
*C40B 50/06* (2006.01)
*C12N 15/10* (2006.01)
*C12N 15/86* (2006.01)
*C07K 14/005* (2006.01)

(52) U.S. Cl.
CPC ........ *C12N 15/1037* (2013.01); *C07K 14/005* (2013.01); *C12N 15/1082* (2013.01); *C12N 15/1086* (2013.01); *C12N 15/86* (2013.01); *C12N 2750/14122* (2013.01); *C12N 2750/14143* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 4,874,237 A | 10/1989 | Cringle |
| 5,219,401 A | 6/1993 | Cathignol et al. |
| 5,383,917 A | 1/1995 | Desai et al. |
| 5,436,146 A | 7/1995 | Shenk et al. |
| 5,527,533 A | 6/1996 | Tso et al. |
| 5,641,749 A | 6/1997 | Yan et al. |
| 5,712,380 A | 1/1998 | Kendall et al. |
| 5,753,500 A | 5/1998 | Shenk et al. |
| 5,792,845 A | 8/1998 | O'Reilly et al. |
| 5,814,618 A | 9/1998 | Bujard et al. |
| 5,861,484 A | 1/1999 | Kendall et al. |
| 5,994,136 A | 11/1999 | Naldini et al. |

(Continued)

FOREIGN PATENT DOCUMENTS

| | | |
|---|---|---|
| EP | 0407122 | 1/1991 |
| EP | 2292781 | 3/2011 |

(Continued)

OTHER PUBLICATIONS

U.S. Appl. No. 13/395,609 (abandoned).

(Continued)

*Primary Examiner* — Christian C Boesen
(74) *Attorney, Agent, or Firm* — Cooley LLP

(57) ABSTRACT

Provided are mutant viral capsid cell libraries, individual cells of such libraries, systems, vectors, and methods for generating the cell libraries, and methods of use thereof to screen for mutant viral capsids with desired characteristics.

20 Claims, 3 Drawing Sheets

Specification includes a Sequence Listing.

(56) References Cited

U.S. PATENT DOCUMENTS

| | | |
|---|---|---|
| 6,013,516 A | 1/2000 | Verma et al. |
| 6,040,183 A | 3/2000 | Ferrari et al. |
| 6,054,485 A | 4/2000 | Schwartz et al. |
| 6,093,570 A | 7/2000 | Ferrari et al. |
| 6,132,732 A | 10/2000 | Young et al. |
| 6,153,436 A | 11/2000 | Hermonat et al. |
| 6,287,815 B1 | 9/2001 | Brown |
| 6,329,181 B1 | 12/2001 | Xiao et al. |
| 6,387,670 B1 | 5/2002 | Leblois-Prehaud et al. |
| 6,458,157 B1 | 10/2002 | Suaning |
| 6,482,634 B1 | 11/2002 | Wilson et al. |
| 6,548,286 B1 | 4/2003 | Samulski et al. |
| 6,723,551 B2 | 4/2004 | Kotin et al. |
| 6,943,153 B1 | 9/2005 | Manning, Jr. et al. |
| 7,070,959 B1 | 7/2006 | Papadopoulos et al. |
| 7,071,159 B2 | 7/2006 | Kendall et al. |
| 7,220,577 B2 | 5/2007 | Zolotukhin |
| 7,585,676 B2 | 9/2009 | Mitrophanous et al. |
| 7,635,474 B2 | 12/2009 | Daly et al. |
| 7,666,405 B2 | 2/2010 | Amalfitano et al. |
| 7,858,367 B2 | 12/2010 | Amalfitano et al. |
| 7,972,278 B2 | 7/2011 | Graham et al. |
| 8,075,137 B2 | 12/2011 | Klistorner et al. |
| 8,118,752 B2 | 2/2012 | Helling et al. |
| 8,137,274 B2 | 3/2012 | Weng et al. |
| 8,163,543 B2 | 4/2012 | Urabe et al. |
| 8,343,067 B2 | 1/2013 | Jones et al. |
| 8,663,624 B2 | 3/2014 | Schaffer et al. |
| 8,900,858 B2 | 12/2014 | Trono et al. |
| 9,193,956 B2 | 11/2015 | Schaffer et al. |
| 9,198,595 B2 | 12/2015 | Neitz et al. |
| 9,233,131 B2 | 1/2016 | Schaffer et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 2002/0168342 A1 | 11/2002 | Wang et al. |
| 2002/0194630 A1 | 12/2002 | Manning, Jr. et al. |
| 2003/0087889 A1 | 5/2003 | Strong et al. |
| 2004/0102765 A1 | 5/2004 | Koenig |
| 2004/0234505 A1 | 11/2004 | Naylor et al. |
| 2005/0053922 A1 | 3/2005 | Schaffer et al. |
| 2005/0260203 A1 | 11/2005 | Wiegand et al. |
| 2006/0128020 A1 | 6/2006 | Calos |
| 2006/0166363 A1 | 7/2006 | Zolotukhin et al. |
| 2006/0193830 A1 | 8/2006 | Hauswirth et al. |
| 2006/0234347 A1 | 10/2006 | Harding et al. |
| 2007/0188710 A1 | 8/2007 | Helling et al. |
| 2007/0190028 A1 | 8/2007 | Qu et al. |
| 2007/0190058 A1 | 8/2007 | Shams |
| 2008/0152654 A1 | 6/2008 | Reich |
| 2009/0112201 A1 | 4/2009 | Young |
| 2009/0128776 A1 | 5/2009 | Keating et al. |
| 2009/0191588 A1 | 7/2009 | Hermens et al. |
| 2009/0191597 A1 | 7/2009 | Samulski et al. |
| 2009/0202490 A1 | 8/2009 | Schaffer et al. |
| 2009/0203071 A1 | 8/2009 | Chen |
| 2009/0285826 A1 | 11/2009 | Bonnel et al. |
| 2010/0008170 A1 | 1/2010 | Sato et al. |
| 2010/0081707 A1 | 4/2010 | Ali et al. |
| 2010/0091242 A1 | 4/2010 | Baglini et al. |
| 2010/0272719 A1 | 10/2010 | Yu |
| 2010/0297084 A1 | 11/2010 | Bennett et al. |
| 2011/0001465 A1 | 1/2011 | Sung et al. |
| 2011/0014655 A1 | 1/2011 | Otte et al. |
| 2011/0052678 A1 | 3/2011 | Shantha et al. |
| 2011/0116046 A1 | 5/2011 | Haeri et al. |
| 2011/0136227 A1 | 6/2011 | Bakker et al. |
| 2011/0270256 A1 | 11/2011 | Nelson et al. |
| 2012/0100606 A1 | 4/2012 | Zolotukhin et al. |
| 2012/0141422 A1 | 6/2012 | Barkats |
| 2012/0164106 A1 | 6/2012 | Schaffer et al. |
| 2012/0172419 A1 | 7/2012 | Neitz et al. |
| 2013/0023034 A1 | 1/2013 | Noordman et al. |
| 2013/0031709 A1 | 2/2013 | Chen et al. |
| 2013/0317091 A1 | 11/2013 | Ye et al. |
| 2013/0323302 A1 | 12/2013 | Constable et al. |
| 2014/0242031 A1 | 8/2014 | Schaffer et al. |
| 2014/0275231 A1 | 9/2014 | Boye et al. |
| 2014/0294771 A1 | 10/2014 | Schaffer et al. |
| 2014/0341977 A1 | 11/2014 | Constable et al. |
| 2014/0364338 A1 | 12/2014 | Schaffer et al. |
| 2014/0371438 A1 | 12/2014 | Constable et al. |
| 2015/0004101 A1 | 1/2015 | Constable et al. |
| 2015/0079038 A1 | 3/2015 | Deverman et al. |
| 2015/0111275 A1 | 4/2015 | Palanker et al. |
| 2015/0118201 A1 | 4/2015 | Xiao et al. |
| 2015/0132262 A1 | 5/2015 | Schaffer et al. |
| 2015/0225702 A1 | 8/2015 | Schaffer et al. |
| 2015/0232953 A1 | 8/2015 | Schaffer et al. |
| 2015/0025939 A1 | 9/2015 | Chalberg et al. |
| 2015/0259395 A1 | 9/2015 | Chalberg et al. |
| 2016/0015288 A1 | 1/2016 | Neitz et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |

FOREIGN PATENT DOCUMENTS

| | | |
|---|---|---|
| EP | 2298925 A2 | 3/2011 |
| GB | 2545763 A | 6/2017 |
| JP | H11100327 A | 4/1999 |
| JP | 2002-539176 A | 11/2002 |
| JP | 2002363107 A | 12/2002 |
| WO | WO 1992/008796 A1 | 5/1992 |
| WO | WO 1994/028143 A1 | 12/1994 |
| WO | WO 1995/022618 A1 | 8/1995 |
| WO | WO 1995/026409 A1 | 10/1995 |
| WO | WO 1998/013071 A1 | 4/1998 |
| WO | WO 1998/051323 A1 | 11/1998 |
| WO | WO 1999/014354 A1 | 3/1999 |
| WO | WO 1999/016889 A1 | 4/1999 |
| WO | WO 1999/036511 A2 | 7/1999 |
| WO | WO 1999/045952 A2 | 9/1999 |
| WO | WO 1999/066959 A2 | 12/1999 |
| WO | WO 2000/001815 A2 | 1/2000 |
| WO | WO 2000/015822 A1 | 3/2000 |
| WO | WO 2002/012525 A2 | 2/2002 |
| WO | WO 2002/082904 A2 | 10/2002 |
| WO | WO 2003/080648 A2 | 10/2003 |
| WO | WO 2004/079332 A2 | 9/2004 |
| WO | WO 2005/005610 A2 | 1/2005 |
| WO | WO 2006/110689 A2 | 10/2006 |
| WO | WO 2007/084773 A2 | 7/2007 |
| WO | WO 2007/148971 A2 | 12/2007 |
| WO | WO 2008/142124 A1 | 11/2008 |
| WO | WO 2008/150459 A1 | 12/2008 |
| WO | WO 2009/073551 A2 | 6/2009 |
| WO | WO 2009/104964 A1 | 8/2009 |
| WO | WO 2009/105669 A2 | 8/2009 |
| WO | WO 2010/099960 A2 | 9/2010 |
| WO | WO 2011/020710 A2 | 2/2011 |
| WO | WO 2011/034947 A2 | 3/2011 |
| WO | WO 2011/088081 A1 | 7/2011 |
| WO | WO 2011/112089 A2 | 9/2011 |
| WO | WO 2011/122950 A1 | 10/2011 |
| WO | WO 2011/126808 A2 | 10/2011 |
| WO | WO 2011/137344 A2 | 11/2011 |
| WO | WO 2012/068317 A2 | 5/2012 |
| WO | WO 2012/145601 A2 | 10/2012 |
| WO | WO 2013/173129 A2 | 11/2013 |
| WO | WO 2013/188316 A1 | 12/2013 |
| WO | WO 2014/207190 A1 | 12/2014 |
| WO | WO 2015/048534 A1 | 4/2015 |
| WO | WO 2015/134643 A1 | 9/2015 |
| WO | WO 2015/142941 A1 | 9/2015 |
| WO | WO 2016/141078 A1 | 9/2016 |
| WO | WO 2017/112868 A1 | 6/2017 |

OTHER PUBLICATIONS

U.S. Appl. No. 13/889,275 (abandoned).
U.S. Appl. No. 14/281,749 (pending).

(56) References Cited

OTHER PUBLICATIONS

U.S. Appl. No. 14/281,783 (pending).
U.S. Appl. No. 14/281,765 (abandoned).
U.S. Appl. No. 14/407,054 (pending).
U.S. Appl. No. 14/660,657 (pending).
U.S. Appl. No. 14/837,448 (pending).
Comparison of L-opsin promoter to SEQ ID No. 80. Printed Feb. 2, 2017, in U.S. Appl. No. 14/660,657, 4 pages.
International Search Report and Written Opinion for International Application No. PCT/US2016/068312, dated May 3, 2017, 22 pages.
Mancuso et al., "Gene therapy treatment of color blindness in adult primates." Journal of Vision (2007); 7(15): 15a. (Abstract).
U.S. Appl. No. 14/444,347, filed Jul. 28, 2014, Schaffer et al.
U.S. Appl. No. 14/444,375, filed Jul. 28, 2014, Schaffer et al.
U.S. Appl. No. 14/606,543, filed Jan. 27, 2015, Schaffer et al.
U.S. Appl. No. 14/938,154, filed Nov. 11, 2015, Schaffer et al.
U.S. Appl. No. 15/229,699, filed Aug. 5, 2016, Schaffer et al.
U.S. Appl. No. 15/244,884, filed Aug. 23, 2016, Schaffer et al.
U.S. Appl. No. 15/244,892, filed Aug. 23, 2016, Schaffer et al.
Albert, Henrik, et al. "Site-specific integration of DNA into wild-type and mutant lox sites placed in the plant genome." The Plant Journal (1995); 7.4: 649-659.
Belteki, Gusztav, et al. "Site-specific cassette exchange and germline transmission with mouse ES cells expressing φC31 integrase." Nature Biotechnology (2003); 21.3: 321-324.
Bethke, Bruce, and Sauer, Brian. "Segmental genomic replacement by Cre-mediated recombination: genotoxic stress activation of the p53 promoter in single-copy transformants." Nucleic Acids Research (1997); 25.14: 2828-2834.
Bi, Yanzhen, et al. "Pseudo attP sites in favor of transgene integration and expression in cultured porcine cells identified by streptomyces phage phiC31 integrase." BMC Molecular Biology (2013); 14: 20, 12 pages.
Calcedo, Roberto, et al. "Worldwide epidemiology of neutralizing antibodies to adeno-associated viruses." Journal of Infectious Diseases (2009); 199.3: 381-390.
Calos, Michele P. "The φC31 Integrase System for Gene Therapy." Current Gene Therapy (2006); 6.6: 633-645.
Chalberg, Thomas W., et al. "Integration specificity of phage φC31 integrase in the human genome." Journal of Molecular Biology (2006); 357.1: 28-48.
Chalberg, Thomas W., et al. "φC31 integrase confers genomic integration and long-term transgene expression in rat retina." Investigative Ophthalmology & Visual Science (2005); 46.6: 2140-2146.
Dalkara, Deniz, et al. "In vivo-directed evolution of a new adeno-associated virus for therapeutic outer retinal gene delivery from the vitreous." Science Translational Medicine (2013); 5.189: 189ra76-189ra76.
Dull, et al., "A third-generation lentivirus vector with a conditional packaging system." Journal of Virology (1998), 72(11):8463-8671.
Groth, Amy C., et al. "A phage integrase directs efficient site-specific integration in human cells." Proc Natl Acad Sci U S A. (2000); 97.11: 5995-6000.
Heinis, Christian, and Johnsson, Kai. "Using peptide loop insertion mutagenesis for the evolution of proteins." Methods Mol Biol. (2010); 634: 217-232.
Hoess, R.H. et al. "The role of the loxP spacer region in P1 site-specific recombination." Nucleic Acids Research (1986); 14.5: 2287-2300.
Kvaratskhelia, Mamuka, et al. "Molecular mechanisms of retroviral integration site selection." Nucleic Acids Research (2014); 42.16: 10209-10225.
Langer, Stephen J., et al. "A genetic screen identifies novel non-compatible loxP sites." Nucleic Acids Research (2002); 30.14: 3067-3077.
Lee, Gwang, and Saito, Izumu. "Role of nucleotide sequences of loxP spacer region in Cre-mediated recombination." Gene (1998); 216.1: 55-65.

Liu, Xiaomei, Han Ping, and Chun Zhang. "Rapid establishment of a HEK 293 cell line expressing FVIII-BDD using AAV site-specific integration plasmids." BMC Research Notes (2014); 7: 626, 6 pages.
Maheshri, Narendra, et al. "Directed evolution of adeno-associated virus yields enhanced gene delivery vectors." Nature Biotechnology (2006); 24.2: 198-204.
McLeod, Maureen, et al. "Identification of the crossover site during FLP-mediated recombination in the Saccharomyces cerevisiae plasmid 2 microns circle." Molecular and Cellular Biology (1986); 6.10: 3357-3367.
Müller, Oliver J., et al. "Random peptide libraries displayed on adeno-associated virus to select for targeted gene therapy vectors." Nature Biotechnology (2003); 21.9: 1040-1046.
Naldini, L., et al., "Efficient transfer, integration, and sustained long-term expression of the transgene in adult rat brains injected with a lentiviral vector." Proc. Natl. Acad. Sci. USA (1996), 93(21): 11382-11388.
Naldini, L., et al., "In vivo gene delivery and stable transduction of nondividing cells by a lentiviral vector." Science (1996), 272(5259): 263-267.
Naldini, L., et al., "Lentiviruses as gene transfer agents for delivery to non-dividing cells." Curr Opin Biotechnol. (1998), 5: 457-463.
Rapti, Kleopatra, et al. "Neutralizing antibodies against AAV serotypes 1, 2, 6, and 9 in sera of commonly used animal models." Molecular Therapy (2012); 20.1: 73-83.
Recchia, Alessandra, et al. "Site-specific integration of functional transgenes into the human genome by adeno/AAV hybrid vectors." Molecular Therapy (2004); 10.4: 660-670.
Sauer, Brian. "Site-specific recombination: developments and applications." Current Opinion in Biotechnology (1994); 5.5: 521-527.
Schlake, Thomas, and Bode, Juergen. "Use of mutated FLP recognition target (FRT) sites for the exchange of expression cassettes at defined chromosomal loci." Biochemistry (1994); 33.43: 12746-12751.
Schmidt, Michael, Sandra Afione, and Robert M. Kotin. "Adeno-associated virus type 2 Rep78 induces apoptosis through caspase activation independently of p53." Journal of Virology (2000); 74.20: 9441-9450.
Senecoff, Julie F., et al. "DNA recognition by the FLP recombinase of the yeast 2 μ plasmid: a mutational analysis of the FLP binding site." Journal of Molecular Biology (1988); 201.2: 405-421.
Thyagarajan, Bhaskar, et al. "Site-specific genomic integration in mammalian cells mediated by phage φC31 integrase." Molecular and Cellular Biology (2001); 21.12: 3926-3934.
Xu, Zhengyao, et al. "Accuracy and efficiency define Bxb1 integrase as the best of fifteen candidate serine recombinases for the integration of DNA into the human genome." BMC Biotechnology (2013); 13: 87, 17 pages.
Zufferey, et al., "Multiply attenuated lentiviral vector achieves efficient gene delivery in vivo." Nat Biotechnol. (1997), 15(9): 871-875.
GenBank [online], Accession No. U47119.2, "Cloning vector pCI, mammalian expression vector." May 10, 2004—uploaded, [retrieved on Apr. 12, 2017], https://www.ncbi.nlm.nih.gov/nuccore/U47119, 2 pages.
Lu, et al., "Complete correction of hemophilia A with adeno-associated viral vectors containing a full-size expression cassette." Hum Gene Ther. (2008); 19(6):648-654. doi: 10.1089/hum.2007.0182.
Samulski, Richard Jude, et al. "Helper-Free Stocks of Recombinant Adeno-Associated Viruses: Normal Integration Does Not Require Viral Gene Expression." Journal of Virology (1989); 63.9: 3822-3828.
Stieger, et al., "AAV-mediated gene therapy for retinal disorders in large animal models." ILAR J. (2009); 50(2): 206-224.
Acland, et al., "Long-term restoration of rod and cone vision by single dose rAAV mediated gene transfer to the retina in a canine model of childhood blindness." Mol Ther. 2005; 12(6): 1072-1082.
Adamis, et al., "Inhibition of vascular endothelial growth factor prevents retinal ischemia-associated iris neovascularization in a nonhuman primate." Arch Ophthalmol. 1996; 114(1): 66-71.

(56) References Cited

OTHER PUBLICATIONS

Adhi, et al., Optical coherence tomography—current and future applications. Curr Opin Ophthalmol. 2013; 24(3): 213-221.
Aflibercept FDA Entry and Label, 2015. 28 pages. downloaded from http://www.accessdata.fda.gov/scripts/cder/drugsatfda/index.cfm?fuseaction=Search.Labei_ApprovaiHistory-#apphist.
Aiello, et al., "Suppression of retinal neovascularization in vivo by inhibition of vascular endothelial growth factor (VEGF) using soluble VEGF-receptor chimeric proteins." Proc Natl Acad Sci USA. 1995; 92(23):10457-10461.
Akimoto, et al., "Adenovirally expressed basic fibroblast growth factor rescues photoreceptor cells in RCS rats." Invest Ophthalmol Vis Sci. 1999; 40(2): 273-279.
Alexander, John J., et al. "Restoration of cone vision in a mouse model of achromatopsia." Nature Medicine (2007); 13.6: 685-687.
Ali, et al., "Gene therapy for inherited retinal degeneration." Br J Ophthalmol. 1997; 81(9): 795-801.
Amado, et al., "Safety and efficacy of subretinal readministration of a viral vector in large animals to treat congenital blindness." Sci Transl Med. 2010; 2(21): 21ra16. doi: 10.1126/scitranslmed.3000659.
Anand, et al., "A deviant immune response to viral proteins and transgene product is generated on subretinal administration of adenovirus and adena-associated virus." Mol Ther. 2002; 5(2):125-132.
Arnold, et al., "Extracts from "clinical evidence": age related macular degeneration." BMJ. 2000; 321(7263):741-744.
Auricchio, et al., "Exchange of surface proteins impacts on viral vector cellular specificity and transduction characteristics: the retina as a model." Hum Mol Genet. 2001; 10(26): 3075-3081.
Auricchio, et al., "Inhibition of retinal neovascularization by intraocular viral-mediated delivery of anti-angiogenic agents." Mol Ther. 2002; 6(4): 490-494.
Bailey, et al., "Exercise increases soluble vascular endothelial growth factor receptor-1 (sFlt-1) in circulation of healthy volunteers." Med Sci Monit. 2006; 12(2): CR45-50.
Bainbridge, et al., "Effect of gene therapy on visual function in Leber's congenital amaurosis." N Engl J Med. 2008; 358(21): 2231-2239.
Bainbridge, et al., "Inhibition of retinal neovascularisation by gene transfer of soluble VEGF receptor sFlt-1." Gene Ther. 2002; 9(5): 320-326.
Bainbridge, J. W., and Ali, R. R. "The eyes have it! Ocular gene therapy trials for LCA look promising." Gene Ther (2008); 15: 1191-1192.
Barleon, et al., "Mapping of the sites for ligand binding and receptor dimerization at the extracellular domain of the vascular endothelial growth factor receptor FLT -1." J Biol Chem. 1997; 272(16):10382-10388.
Barleon, et al., "Soluble VEGFR-1 secreted by endothelial cells and monocytes is present in human serum and plasma from healthy donors." Angiogenesis. 2001; 4(2):143-154.
Belgore, et al., "Plasma levels of vascular endothelial growth factor (VEGF) and its receptor, Flt-1, in haematological cancers: a comparison with breast cancer." Am J Hematol. 2001; 66(1): 59-61.
Bennett, "Immune response following intraocular delivery of recombinant viral vectors." Gene Ther. 2003; 10(11): 977-982.
Bennett, et al., "AAV2 gene therapy readministration in three adults with congenital blindness." Sci Transl Med. 2012; 4(120): 120ra15.
Bennett, et al., "Gene therapy for retinitis pigmentosa." Curr Opin Mol Ther. 2000; 2(4): 420-5.
Bennicelli, et al., "Reversal of blindness in animal models of leber congenital amaurosis using optimized AAV2-mediated gene transfer." Mol Ther. 2008; 16(3): 458-465.
Berge, et al., "Pharmaceutical salts." J Pharm Sci. 1977; 66(1): 1-19.
Bhisitkul, "Vascular endothelial growth factor biology: clinical implications for ocular treatments." Br J Ophthalmol. 2006; 90(12): 1542-1547.
Brinkmann, et al., "Origin of retinal pigment epithelium cell damage by pulsed laser irradiance in the nanosecond to microsecond time regimen." Laser Surg Med. 2000; 27: 451-464.
Brinkmann, et al., "Selective retina therapy (SRT): a review on methods, techniques, preclinical and first clinical results." Bull Soc Beige Ophtalmol. 2006; 302: 51-69.
Brown, et al., "Ranibizumab versus verteporfin photodynamic therapy for neovascular age-related macular degeneration: Two-year results of the ANCHOR study." Ophthalmology. 2009; 116(1): 57-65.
Büning, Hildegard, et al. "Recent developments in adeno-associated virus vector technology." The Journal of Gene Medicine (2008); 10.7: 717-733.
Cai, Xue, et al. "Gene delivery to mitotic and postmitotic photoreceptors via compacted DNA nanoparticles results in improved phenotype in a mouse model of retinitis pigmentosa." The FASEB Journal (2010); 24.4: 1178-1191.
Campochiaro, "Molecular targets for retinal vascular diseases." J Cell Physiol. 2007; 210(3): 575-581.
Campochiaro, "Gene Transfer for Neovascular Age-Related Macular Degeneration." Human Gene Therapy (2011); 22(5): 523-529.
Campochiaro, et al., "Adenoviral vector-delivered pigment epithelium-derived factor for neovascular age-related macular degeneration: results of a phase I clinical trial." Hum Gene Ther. 2006; 17(2): 167-176.
Campochiaro, et al., "Monitoring ocular drug therapy by analysis of aqueous samples." Ophthalmology. 2009; 116(11): 2158-2164.
Cao, et al., "A subretinal matrigel rat choroidal neovascularization (CNV) model and inhibition of CNV and associated inflammation and fibrosis by VEGF trap." Invest Ophthalmol Vis Sci. 2010; 51(11): 6009-6017.
Cayouette, et al., "Adenovirus-mediated gene transfer of ciliary neurotrophic factor can prevent photoreceptor degeneration in the retinal degeneration (rd) mouse." Hum Gene Ther. 1997; 8(4): 423-430.
Chakrabarti, et al., "Normal T-cell turnover in sooty mangabeys harboring active simian immunodeficiency virus infection." J Virol. 2000; 74(3): 1209-1223.
Chalberg, et al., "φC31 integrase confers genomic integration and long-term transgene expression in rat retina." Invest Ophthalmol Vis Sci. 2005; 46(6): 2140-2146.
Chen, et al., "Use of nepafenac (Nevanac) in combination with intravitreal anti-VEGF agents in the treatment of recalcitrant exudative macular degeneration requiring monthly injections." Clin Ophthalmol. 2010; 4:1249-1252.
Chiu, M. I., and Nathans, J. "Blue cones and cone bipolar cells share transcriptional specificity as determined by expression of human blue visual pigment-derived transgenes." The Journal of Neuroscience (1994); 14.6: 3426-3436.
Choi, et al., "Production of recombinant adena-associated viral vectors." Curr Protoc Hum Genet. 2007; Chapter 12: Unit 12.9.doi: 10.1002/0471142905.hg1209s53.
Chung, et al., "Angiogenesis in myocardial infarction. An acute or chronic process?" Eur Heart J. 2002; 23(20): 1604-1608.
Cideciyan, Artur V., et al. "Human gene therapy for RPE65 isomerase deficiency activates the retinoid cycle of vision but with slow rod kinetics." Proceedings of the National Academy of Sciences (2008); 105.39: 15112-15117.
Cideciyan, et al., "Human RPE65 gene therapy for Leber congenital amaurosis: persistence of early visual improvements and safety at 1 year." Hum Gene Ther. 2009; 20(9): 999-1004.
Clark, et al., "Expression of clusterin/sulfated glycoprotein-2 under conditions of heat stress in rat Sertoli cells and a mouse Sertoli cell line." J Androl. 1997; 18(3): 257-63.
Clinical trial, A Phase I/II Controlled Dose-escalating Trial to Establish the Baseline Safety and Efficacy of a Single SubretinalInjection of rAAV.sFit-1 Into Eyes of Patients With Exudative Age-related Macular Degeneration (AMD). NCT01494805. Dec. 16, 2011.
Clinical trial. Safety and Tolerability Study of AAV2-sFLT-1 in Patients With Neovascular Age-Related Macular Degeneration (AMD). NCT01024998. Last updated: Jan. 28, 2014.

(56) References Cited

OTHER PUBLICATIONS

Csermely, et al., "The 90-kDa molecular chaperone family: structure, function, and clinical applications." A comprehensive review. Pharmacol Ther. 1998; 79(2):129-168.
Curtis, et al., "Risks of mortality, myocardial infarction, bleeding, and stroke associated with therapies for age-related macular degeneration." Arch Ophthalmol. 2010; 128(10): 1273-1279.
Dalkara, et al., "In vivo-directed evolution of a new adeno-associated virus for therapeutic outer retinal gene delivery from the vitreous." Sci Transl Med. 2013; 5(189): 189ra76.
Davidson, et al., "A model system for in vivo gene transfer into the central nervous system using an adenoviral vector." Nat Genet. 1993; 3(3): 219-223.
Davis, et al., "Direct gene transfer into skeletal muscle in vivo: factors affecting efficiency of transfer and stability of expression." Hum Gene Ther. 1993; 4(2): 151-159.
Dawson, et al., "Pigment epithelium-derived factor: a potent inhibitor of angiogenesis." Science. 1999; 285(5425): 245-248.
De Vries, et al., "The fms-like tyrosine kinase, a receptor for vascular endothelial growth factor." Science. 1992; 255(5047): 989-991.
Dejneka, et al., "Gene therapy and animal models for retinal disease." Dev Ophthalmol. 2003; 37: 188-198.
Dejneka, et al., "Gene therapy and retinitis pigmentosa: advances and future challenges." Bioessays 2001; 23(7): 662-8.
Deonarain, M.P., "Ligand-targeted receptor-mediated vectors for gene delivery", Expert Opinion on Therapeutic Patents. 1998; 8: 53-69.
DeValois, R.L. and DeValois, K.K. "A multi-stage color model." Vision Research (1993); 33.8: 1053-1065.
Diab, et al., "Angiogenic factors for the prediction of pre-eclampsia in women with abnormal midtrimester uterine artery Doppler velocimetry." Int J Gynaecol Obstet. 2008; 102(2):146-151.
Dudus, et al., "Persistent trans gene product in retina, optic nerve and brain after intraocular injection of rAAV." Vision Res. 1999; 39(15): 2545-2553.
Easton, et al., "The Hsp110 and Grp170 stress proteins: newly recognized relatives of the Hsp70s." Cell Stress Chaperones. 2000; 5(4): 276-290.
Edelstein et al., "Gene therapy clinical trials worldwide 1989-2004—an overview", Journal Gene Med. (2004); 6: 597-602.
European Patent Application No. 13791695.3, Extended European Search Report dated Dec. 21, 2015, 10 pages.
Excoffon, et al., "Directed evolution of adeno-associated virus to an infectious respiratory virus." Proc Natl Acad Sci U S A. 2009; 106(10): 3865-3870.
Ferrara, "Vascular endothelial growth factor: basic science and clinical progress." Endocr Rev. 2004; 25(4): 581-611.
Fong, et al., "The use and development of retroviral vectors to deliver cytokine genes for cancer therapy." Crit Rev Ther Drug Carrier Syst. 2000; 17(1): 1-60.
Fotsis, et al., "The endogenous oestrogen metabolite 2-methoxyoestradiol inhibits angiogenesis and suppresses tumour growth." Nature. 1994; 368(6468): 237-239.
Framme, et al., "Selective targeting of the retinal pigment epithelium in rabbit eyes with a scanning laser beam." Investigative Ophthalmology & Visual Science. 2007; 48(4): 1782-92.
Funk, et al., "Neovascular age-related macular degeneration: intraocular cytokines and growth factors and the influence of therapy with ranibizumab." Ophthalmology. 2009; 116(12): 2393-2399.
Galan, et al., "Association of age-related macular degeneration with polymorphisms in vascular endothelial growth factor and its receptor." Ophthalmology. 2010; 117(9): 1769-1774.
Geller, et al., "An HSV-1 vector expressing tyrosine hydroxylase causes production and release of L-dopa from cultured rat striatal cells." J Neurochem. 1995; 64(2):487-496.
Geller, et al., "Infection of cultured central nervous system neurons with a defective herpes simplex virus 1 vector results in stable expression of Escherichia coli beta-galactosidase." Proc Natl Acad Sci USA. 1990; 87(3): 1149-1153.

Geller, et al., "Long-term increases in neurotransmitter release from neuronal cells expressing a constitutively active adenylate cyclase from a herpes simplex virus type 1 vector." Proc Natl Acad Sci USA. 1993; 90(16): 7603-7607.
Gerdes, et al., "Cell cycle analysis of a cell proliferation-associated human nuclear antigen defined by the monoclonal antibody Ki-67." J Immunol. 1984; 133(4):1710-1715.
Glushakova, Lyudmyla G., et al. "Human blue-opsin promoter preferentially targets reporter gene expression to rat s-cone photoreceptors." Investigative Ophthalmology & Visual Science (2006); 47.8: 3505-3513.
Goldman, et al., "Paracrine expression of a native soluble vascular endothelial growth factor receptor inhibits tumor growth, metastasis, and mortality rate." Proc Natl Acad Sci USA. 1998; 95(15): 8795-8800.
Goverdhana, et al., Regulatable gene expression systems for gene therapy applications: progress and future challenges. Molecular Therapy : The Journal of the American Society of Gene Therapy. 2005; 12(2): 189-211.
Gragoudas, et al., "Pegaptanib for neovascular age-related macular degeneration." N Engl J Med. 2004; 351(27): 2805-2816.
Graubert, et al., "Vascular repair after menstruation involves regulation of vascular endothelial growth factor-receptor phosphorylation by sFLT-1." Am J Pathol. 2001; 158(4): 1399-1410.
Gray and Zolotukhin, "Design and Construction of Functional AAV Vectors." Methods in Molecular Biology. 2011; 807: 25-46.
Gunther, Karen L., et al. "A novel mutation in the short-wavelength-sensitive cone pigment gene associated with a tritan color vision defect." Visual Neuroscience (2006); 23.3-4: 403-409.
Hasumi, et al., "Soluble FLT-1 expression suppresses carcinomatous ascites in nude mice bearing ovarian cancer." Cancer Res. 2002; 62(7): 2019-2023.
Hauswirth, et al., "Treatment of leber congenital amaurosis due to RPE65 mutations by ocular subretinal injection of adena-associated virus gene vector: short-term results of a phase I trial." Hum Gene Ther. 2008; 19(10): 979-990.
He, et al., "Alternative splicing of vascular endothelial growth factor (VEGF)-R1 (FLT-1) pre-mRNA is important for the regulation of VEGF activity." Mol Endocrinol. 1999; 13(4): 537-545.
Hoffman, et al., "Cell-mediated immune response and stability of intraocular transgene expression after adenovirus-mediated delivery." Invest Ophthalmol Vis Sci. 1997; 38(11): 2224-2233.
Honda, et al., "Experimental subretinal neovascularization is inhibited by adenovirus-mediated soluble VEGF/flt-1 receptor gene transfection: a role of VEGF and possible treatment for SRN in age-related macular degeneration." Gene Ther. 2000; 7(11): 978-985.
Hu, et al., "Design of retroviral vectors and helper cells for gene therapy." Pharmacol Rev. 2000; 52(4): 493-511.
Huang, et al., "Innate immune recognition of viruses and viral vectors." Hum Gene Ther. 2009; 20(4): 293-301.
Ibrahim, et al., "Heat shock and arsenite induce expression of the nonclassical class I histocompatibility HLA-G gene in tumor cell lines." Cell Stress Chaperones. 2000; 5(3): 207-18.
International Preliminary Report on Patentability for International Application No. PCT/US2010/048964, dated Mar. 20, 2012, 14 pages.
International Preliminary Report on Patentability for International Application No. PCT/US2013/040011, dated Nov. 18, 2014, 2013, 48 pages.
International Preliminary Report on Patentability for International Application No. PCT/US2013/045043, dated Nov. 12, 2013, 11 pages.
International Preliminary Report on Patentability for International Application No. PCT/US2015/021087, dated Sep. 20, 2016, 8 pages.
International Search Report and Written Opinion for International Application No. PCT/US2010/048964, dated Jun. 17, 2011, 23 pages.
International Search Report and Written Opinion for International Application No. PCT/US2013/040011, dated Dec. 17, 2013, 57 pages.

(56) References Cited

OTHER PUBLICATIONS

International Search Report and Written Opinion for International Application No. PCT/US2013/045043, dated Nov. 12, 2013, 11 pages.
International Search Report and Written Opinion for International Application No. PCT/US2015/021087, dated Aug. 12, 2015, 12 pages.
International Search Report and Written Opinion for International Application No. PCT/US2016/020482, dated Aug. 8, 2016, 12 pages.
Jacobs, Gerald H. "A perspective on color vision in platyrrhine monkeys." Vision Research (1998); 38.21: 3307-3313.
Jacobs, Gerald H., et al. "Emergence of novel color vision in mice engineered to express a human cone photopigment." Science (2007); 315.5819: 1723-1725.
Jacobson, et al., "Gene therapy for leber congenital amaurosis caused by RPE65 mutations: safety and efficacy in 15 children and adults followed up to 3 years." Arch Ophthalmol. 2012;130(1): 9-24.
Jacobson, et al., "Safety in nonhuman primates of ocular AAV2-RPE65, a candidate treatment for blindness in Leber congenital amaurosis." Hum Gene Ther. 2006; 17(8): 845-858.
Jacobson, et al., "Safety of recombinant adena-associated virus type 2-RPE65 vector delivered by ocular subretinal injection", Mol Ther. (2006); 13(6):1074-1084.
Johnson-Saliba and Jans, "Gene Therapy: Optimising DNA Delivery to the Nucleus", Curr. Drug. Targets 2001; 2(4): 371-399.
Kaplitt, et al., "Long-term gene expression and phenotypic correction using adeno associated virus vectors in the mammalian brain." Nat Genet. 1994; 8(2):148-154.
Kendall, et al., "Identification of a natural soluble form of the vascular endothelial growth factor receptor, FLT-1, and its heterodimerization with KDR." Biochem Biophys Res Commun. 1996; 226(2): 324-328.
Kendall, et al., "Inhibition of vascular endothelial cell growth factor activity by an endogenously encoded soluble receptor." Proc Natl Acad Sci USA. 1993; 90(22):10705-10709.
Khaliq, et al., "Increased expression of placenta growth factor in proliferative diabetic retinopathy." Lab Invest. 1998; 78(1): 109-116.
Khani, et al., "AAV-mediated expression targeting of rod and cone photoreceptors with a human rhodopsin kinase promoter." Investigative Ophthalmology & Visual Science. 2007; 48(9): 3954-61.
Kiang, et al., "Cytoprotection and regulation of heat shock proteins induced by heat shock in human breast cancer T47-D cells: role of [Ca2+]i and protein kinases." FASEB J. 1998; 12(14): 1571-1579.
Klein, et al., "Fifteen-year cumulative incidence of age-related macular degeneration: the Beaver Dam Eye Study." Ophthalmology. 2007; 114(2): 253-262.
Klein, et al., "The relation of cardiovascular disease and its risk factors to the 5-year incidence of age-related maculopathy: the Beaver Dam Eye Study." Ophthalmology. 1997; 104(11): 1804-1812.
Kliffen, et al., "Increased expression of angiogenic growth factors in age-related maculopathy." Br J Ophthalmol. 1997; 81(2): 154-162.
Klimczak, et al., "A novel adeno-associated viral variant for efficient and selective intravitreal transduction of rat Müller cells." PLoS One. 2009; 4(10): e7467.
Komáromy, András M., et al. "Gene therapy rescues cone function in congenital achromatopsia." Human Molecular Genetics (2010): ddq136., 13 pages.
Komaromy, et al., "Targeting gene expression to cones with human cone opsin promoters in recombinant AAV." Gene Ther. 2008; 15(14): 1049-1055.
Kong, et al., "Regional suppression of tumor growth by in vivo transfer of a cDNA encoding a secreted form of the extracellular domain of the flt-1 vascular endothelial growth factor receptor." Hum Gene Ther. 1998; 9(6): 823-833.

Kozak. "Point mutations define a sequence flanking the AUG initiator codon that modulates translation by eukaryotic ribosomes", Cell (1986); 44(2): 283-292 (Abstract Only).
Krysiak, et al., "Soluble vascular endothelial growth factor receptor-1 (sFLT-1) mediates downregulation of FLT-1 and prevents activated neutrophils from women with preeclampsia from additional migration by VEGF." Circ Res. 2005; 97(12): 1253-1261.
Krzystolik, et al., "Prevention of experimental choroidal neovascularization with intravitreal anti-vascular endothelial growth factor antibody fragment." Arch Ophthalmol. 2002; 120(3):338-346.
Kuchenbecker, James A., et al. "Topography of the long-to middle-wavelength sensitive cone ratio in the human retina assessed with a wide-field color multifocal electroretinogram." Visual Neuroscience (2008); 25.03: 301-306.
Kvanta, et al., "Subfoveal fibrovascular membranes in age-related macular degeneration express vascular endothelial growth factor." Invest Ophthalmol Vis Sci. 1996; 37(9): 1929-1934.
Kwak, et al., "VEGF is major stimulator in model of choroidal neovascularization." Invest Ophthalmol Vis Sci. 2000; 41(10): 3158-3164.
Lai, et al., "Generation of transgenic mice with mild and severe retinal neovascularisation." Br J Ophthalmol. 2005; 89(7): 911-916.
Lai, et al., "Inhibition of angiogenesis by adenovirus-mediated sFlt-1 expression in a rat model of corneal neovascularization." Hum Gene Ther. 2001; 12(10): 1299-1310.
Lai, et al., "Long-term Evaluation of AAV -Mediated sFlt-1 Gene Therapy for Ocular Neovascularization in Mice and Monkeys." Mol Ther. 2005; 12(4): 659-668.
Lai, et al., "Potential long-term inhibition of ocular neovascularisation by recombinant adena-associated virus-mediated secretion gene therapy." Gene Ther. 2002; 9(12): 804-813.
Lai, et al., "Preclinical safety evaluation of subretinal AAV2.sFlt-1 in non-human primates." Gene Ther. 2012; 19(10): 999-1009.
Lai, et al., "rAAV.sFlt-1 Gene Therapy Achieves Lasting Reversal of Retinal Neovascularization in the Absence of a Strong Immune Response to the Viral Vector." Invest Ophthalmol Vis Sci. 2009; 50(9): 4279-4287.
Lai, et al., "Recombinant adena-associated virus type 2-mediated gene delivery into the Rpe65-/- knockout mouse eye results in limited rescue." Genet Vaccines Ther. 2004; 2:3, 15 pages.
Lai, Timothy YY, et al. "The clinical applications of multifocal electroretinography: a systematic review." Survey of Ophthalmology (2007); 52.1: 61-96.
Lalwani, et al., "A variable-dosing regimen with intravitreal ranibizumab for neovascular age-related macular degeneration: year 2 of the PrONTO Study." Am J Ophthalmol. 2009; 148(1): 43-58.
Lavinksy, D. et al., "Modulation of transgene expression in retinal gene therapy by selective laser treatment." Investigative Ophthalmology & Visual Science. 2013; 54(3): 1873-1880.
Le Gal La Salle, et al., "An adenovirus vector for gene transfer into neurons and glia in the brain." Science. 1993; 259(5097): 988-990.
Le Meur, et al., "Postsurgical assessment and long-term safety of recombinant adeno-associated virus-mediated gene transfer into the retinas of dogs and primates." Arch Ophthalmol. 2005; 123(4): 500-506.
Le Meur, et al., "Restoration of vision in RPE65-deficient Briard dogs using an AAV serotype 4 vector that specifically targets the retinal pigmented epithelium." Gene Ther. 2007; 14(4): 292-303.
Lebherz, et al., "Novel AAV serotypes for improved ocular gene transfer." J Gene Med. 2008; 10(4): 375-382.
Levine, et al., "Circulating angiogenic factors and the risk of preeclampsia." N Engl J Med. 2004; 350(7): 672-683.
Li, et al., "Gene therapy following subretinal AAV5 vector delivery is not affected by a previous intravitreal AAV5 vector administration in the partner eye." Mol Vis. 2009; 15: 267-275.
Li, et al., "Intraocular route of AAV2 vector administration defines humoral immune response and therapeutic potential." Mol Vis. 2008; 14: 1760-1769.
Li, et al., "Cone-specific expression using a human red opsin promoter in recombinant AAV." Vision Res. 2008; 48(3): 332-338.
Lieber, et al., "Integrating adenovirus-adena-associated virus hybrid vectors devoid of all viral genes." J Virol. 1999; 73(11): 9314-9324.

(56) References Cited

OTHER PUBLICATIONS

Lindenberg, Thomas, et al. "Cyclic summation versus m-sequence technique in the multifocal ERG." Graefe's Archive for Clinical and Experimental Ophthalmology (2003); 241.6: 505-510.
Liu, et al., "Soluble Fms-like tyrosine kinase-1 expression inhibits the growth of multiple myeloma in nude mice." Acta Biochim Biophys Sin (Shanghai). 2007; 39(7): 499-506.
Liu, et al., "Gene therapy for ocular diseases." Br J Ophthalmol. 2011; 95(5): 604-612.
Lopez, et al., "Transdifferentiated retinal pigment epithelial cells are immunoreactive for vascular endothelial growth factor in surgically excised age-related macular degeneration-related choroidal neovascular membranes." Invest Ophthalmol Vis Sci. 1996; 37(5): 855-868.
Lukason, et al., "Inhibition of choroidal neovascularization in a nonhuman primate model by intravitreal administration of an AAV2 vector expressing a novel anti-VEGF molecule." Mol Ther. 2011; 19(2): 260-265.
Lundstrom, "Alphavirus vectors: applications for DNA vaccine production and gene expression." Intervirology. 2000; 43(4-6): 247-257.
Luo and Saltzman, "Synthetic DNA delivery systems", Nature Biotechnol. 2000; 18(1): 33-37.
Luthert, et al., "Photoreceptor rescue." Eye (Lond). 1998; 12(Pt 3b): 591-596.
MacLachlan, et al., "Preclinical safety evaluation of AAV2-sFLT01—a gene therapy for age-related macular degeneration." Mol Ther. 2011; 19(2): 326-334.
Mae, et al., "Gene transfer of the vascular endothelial growth factor receptor flt-1 suppresses pulmonary metastasis associated with lung growth." Am J Respir Cell Mol Biol. 2005; 33(6): 629-635.
Maguire, et al., "Age-dependent effects of RPE65 gene therapy for Leber's congenital amaurosis: a phase 1 dose-escalation trial." Lancet. 2009; 374(9701): 1597-1605.
Maguire, et al., "Safety and efficacy of gene transfer for Leber's congenital amaurosis." N Engl J Med. 2008; 358(21): 2240-2248.
Mahasreshti, et al., "Adenovirus-mediated soluble FLT-1 gene therapy for ovarian carcinoma." Clin Cancer Res. 2001; 7(7): 2057-2066.
Mahasreshti, et al., "Intravenous delivery of adenovirus-mediated soluble FLT-1 results in liver toxicity." Clin Cancer Res. 2003; 9(7): 2701-2710.
Makous, Walter. "Comment on "emergence of novel color vision in mice engineered to express a human cone photopigment"." Science (2007); 318.5848: 196b-196b.
Malamos, et al., "Correlation of high-definition optical coherence tomography and fluorescein angiography imaging in neovascular macular degeneration." Invest. Ophthalmol Vis Sci. 2009; 50(10): 4926-4933.
Mancuso, et al. "Recombinant adena-associated virus targets passenger gene expression to cones in primate retina", Journal of the Optical Society of America A (2007); 24(5): 1411-1416.
Mancuso, et al. "Colorblindness Cure: Gene Therapy Confers a New Sensation", Investigative Opthamology & Visual Science (2008); 49:3252 (Meeting Abstract).
Mancuso, K., et al. "Progress in Developing a Gene Therapy Approach for Treating Color Blindness." Investigative Ophthalmology & Visual Science 46.13 (2005): 4565-4565 & 2005 Annual Meeting of the Association for Research in Vision and Ophthalmology, FL. Lauderdale, FL, 46(Supp S): 4565 (2005).
Mancuso, Katherine, et al. "An adaptation of the Cambridge Colour Test for use with animals." Visual Neuroscience (2006); 23.3-4: 695-701.
Mancuso, Katherine, et al. "Gene therapy for red-green colour blindness in adult primates." Nature (2009); 461.7265: 784-787.
Manno, et al., "Successful transduction of liver in hemophilia by AAV-Factor IX and limitations imposed by the host immune response." Nat Med. 2006; 12(3): 342-347.
Martin et al., "Gene delivery to the eye using adeno-associated viral vectors", Methods. 2002; 28: 267-275.
Mauck, M. C., et al. "Longitudinal in vivo Characterization of Expression of Viral Delivered Genes for L-opsin and Green Fluorescent Protein in Cone Photoreceptors of Gerbils." Investigative Ophthalmology & Visual Science (2006); 47.13: 4071-4071.
Mauck, Matthew C., et al. "Longitudinal evaluation of expression of virally delivered transgenes in gerbil cone photoreceptors." Visual Neuroscience (2008); 25.3: 273.
Maynard, et al., "Excess placental soluble fms-like tyrosine kinase 1 (sFlt1) may contribute to endothelial dysfunction, hypertension, and proteinuria in preeclampsia." J Clin Invest. 2003; 111(5): 649-658.
Merigan, et al., "Tracking Transfection of Macaque Retinal Ganglion Cells With AAV2 Viral Vectors; In vivo Imaging Reveals Differences Between Two Promoters." ARVO Annual Meeting Abstract (May 2008); Investigative Ophthalmology & Visual Science. 2008; vol. 49: 4514.
Michel, et al., "Stress-induced transcription of the clusterin/apoJ gene." Biochem J. 1997; 328 ( Pt 1): 45-50.
Miller, et al., "Human effector and memory CD8+ T cell responses to smallpox and yellow fever vaccines." Immunity. 2008; 28(5): 710-722.
Mitchell, et al., "Cost effectiveness of treatments for wet age-related macular degeneration." PharmacoEconomics 2011; 29(2): 107-131.
Mitchell, et al., "Ranibizumab (Lucentis) in neovascular age-related macular degeneration: evidence from clinical trials." Br J Ophthalmol. 2010; 94(1): 2-13.
Miyamoto, et al., "Prevention of leukostasis and vascular leakage in streptozotocininduced diabetic retinopathy via intercellular adhesion molecule-1 inhibition." Proc Natl Acad Sci USA. 1999; 96(19): 10836-10841.
Miyoshi, et al., "Development of a self-inactivating lentivirus vector." J Virol. 1998; 72(10): 8150-8157.
Narfstrom, et al., "Assessment of structure and function over a 3-year period after gene transfer in RPE65-/-dogs." Doc Ophthalmol. 2005; 111(1): 39-48.
Narfstrom, et al., "Functional and structural recovery of the retina after gene therapy in the RPE65 null mutation dog." Invest Ophthalmol Vis Sci. 2003; 44(4):1663-1672.
Narfstrom, et al., "In vivo gene therapy in young and adult RPE65-/-dogs produces long-term visual improvement." J Hered. 2003; 94(1): 31-37.
Nathans, et al., "Molecular genetics of human blue cone monochromacy." Science. 1989; 245(4920): 831-838.
Nathans, J., et al. "Molecular genetics of human color vision: the genes encoding blue, green, and red pigments." Science (1986); 232(4747): 193-202.
Nathans, Jeremy, et al. "Molecular genetics of inherited variation in human color vision." Science (1986); 232.4747: 203-210.
Neitz, Maureen, et al. "Spectral tuning of pigments underlying red-green color vision." Science (1991); 252.5008: 971-974.
Nemerow, "A new link between virus cell entry and inflammation: adenovirus interaction with integrins induces specific pro inflammatory responses." Mol Ther. 2009; 17(9): 1490-1491.
Neufeld, et al., "Vascular endothelial growth factor (VEGF) and its receptors." FASEB J. 1999; 13(1): 9-22.
Niederkorn, et al., "See no evil, hear no evil, do no evil: the lessons of immune privilege." Nat Immunol. 2006; 7(4): 354-359.
Ohno-Matsui, et al., "Novel mechanism for age-related macular degeneration: an equilibrium shift between the angiogenesis factors VEGF and PEDF." J Cell Physiol. 2001; 189(3): 323-333.
Oikawa, et al., "Three novel synthetic retinoids, Re 80, Am 580 and Am 80, all exhibit anti-angiogenic activity in vivo." Eur J Pharmacol. 1993; 249(1): 113-116.
Palu et al., "In pursuit of new developments for gene therapy of human diseases", J. of Biotechnology. 1999; 68: 1-13.
Pang, Ji-jing, et al. "Gene therapy restores vision-dependent behavior as well as retinal structure and function in a mouse model of RPE65 Leber congenital amaurosis." Molecular Therapy (2006); 13.3: 565-572.
Papadakis et al. "Promoters and Control Elements: Designing Expression Cassettes for Gene Therapy." Current Gene Therapy (2004); 4(1): 89-113.

(56) References Cited

OTHER PUBLICATIONS

Park, et al., "The fourth immunoglobulin-like loop in the extracellular domain of FLT-1, a VEGF receptor, includes a major heparin-binding site." Biochem Biophys Res. Commun. 1999; 264(3): 730-734.
Paulus, et al., "Selective retinal therapy with microsecond exposures using a continuous line scanning laser." Retina. 2011; 31(2): 380-388.
Pechan, et al., "Novel anti-VEGF chimeric molecules delivered by AAV vectors for inhibition of retinal neovascularization", Gene Ther. (2009); 16(1): 10-16.
Perri, et al., "Replicon vectors derived from Sindbis virus and Semliki forest virus that establish persistent replication in host cells." J Virol. 2000; 74(20): 9802-9807.
Pfeifer and Verma, "Gene Therapy: Promises and Problems", Annu. Rev. Genomics. Hum. Genet. 2001; 2: 177-211.
Pieramici, et al., "Age-related macular degeneration and risk factors for the development of choroidal neovascularization in the fellow eye." Curr Opin Ophthalmol. 1998; 9(3): 38-46.
Pitcher, et al., "Development and homeostasis of T cell memory in rhesus macaque." J Immunol. 2002; 168(1): 29-43.
Pollock, et al, "Delivery of a stringent dimerizer-regulated gene expression system in a single retroviral vector." Proceedings of the National Academy of Sciences of the United States of America. 2000; 97(24): 13221-6.
Provost, et al., "Biodistribution of rAAV vectors following intraocular administration: evidence for the presence and persistence of vector DNA in the optic nerve and in the brain." Mol Ther. 2005; 11(2): 275-83.
Pshenichkin, et al., "Heat shock enhances CMV—IE promoter-driven metabotropic glutamate receptor expression and toxicity in transfected cells." Neuropharmacology. 2011; 60: 1292-1300.
Quantin, et al., "Adenovirus as an expression vector in muscle cells in vivo." Proc Natl Acad Sci USA. 1992; 89(7): 2581-2584.
Reffin, J. P., et al. "Trials of a computer-controlled colour vision test that preserves the advantages of pseudoisochromatic plates." Colour Vision Deficiencies X. Springer Netherlands (1991); pp. 69-76.
Regan, Benedict C., et al. "Luminance noise and the rapid determination of discrimination ellipses in colour deficiency." Vision Research (1994); 34.10: 1279-1299.
Regeneron press release, Bayer and Regeneron Report Positive Top-Line Results of Two Phase 3 Studies with VEGF Trap-Eye in Wet Age-related Macular Degeneration. Nov. 22, 2010. http://newsroom.regeneron.com/releasedetail.cfm?ReleaseiD=532099 (last accessed Nov. 24, 2010).
Regillo, et al., "Randomized, double-masked, sham-controlled trial of ranibizumab for neovascular age-related macular degeneration: PIER Study year 1." Am J Ophthalmol. 2008; 145(2): 239-248.
Rein, et al., "Forecasting age-related macular degeneration through the year 2050: the potential impact of new treatments." Arch Ophthalmol. 2009; 127(4): 533-540.
Response to request under 27 CFR 1.1 05, dated Apr. 27, 2015, in U.S. Appl. No. 10/075,415, pp. 8-10 (3 pages).
Roberts, et al., "Pathogenesis and genetics of pre-eclampsia." Lancet. 2001; 357(9249): 53-56.
Robinson, et al., "The splice variants of vascular endothelial growth factor (VEGF) and their receptors." J Cell Sci. 2001; 114(Pt 5): 853-865.
Rolling, et al., "Long-term real-time monitoring of adena-associated virus-mediated gene expression in the rat retina." Clin Experiment Ophthalmol. 2000; 28(5): 382-386.
Romano, et al., "Latest developments in gene transfer technology: achievements, perspectives, and controversies over therapeutic applications." Stem Cells. 2000; 18(1): 19-39.
Rome, C., et al., "Spatial and temporal control of expression of therapeutic genes using heat shock protein promoters." Methods (2005); 35.2: 188-198.
Rosenfeld, et al., "In vivo transfer of the human cystic fibrosis transmembrane conductance regulator gene to the airway epithelium." Cell. 1992; 68(1): 143-155.
Rosenfeld, et al., "Ranibizumab for neovascular age-related macular degeneration." N Engl J Med. 2006; 355(14): 1419-1431.
Saishin, et al., "VEGF-TRAP(R1R2) suppresses choroidal neovascularization and VEGF-induced breakdown of the blood-retinal barrier." J Cell Physiol. 2003; 195(2): 241-248.
Salam, et al., "Treatment of proliferative diabetic retinopathy with anti-VEGF agents." Acta Ophthalmol. 2011; 89(5): 405-411.
Schmidt-Erfurth, "Clinical safety of ranibizumab in age-related macular degeneration." Expert Opin Drug Saf. 2010; 9(1):149-165.
Schmidt-Erfurth, et al., "Efficacy and safety of monthly versus quarterly ranibizumab treatment in neovascular age-related macular degeneration: the EXCITE study." Ophthalmology. 2011; 118(5): 831-839.
Schuele, et al., "RPE damage thresholds and mechanisms for laser exposure in the microsecond-to-millisecond time regimen." Invest Ophthalmol Vis Sci. 2005; 46: 714-719.
Schwartz, et al., "Embryonic stem cell trials for macular degeneration: a preliminary report." Lancet. 2012; 379(9817): 713-720.
Search Report (English translation) in Chinese Application No. 2013800375773, dated Nov. 24, 2016, 2 pages.
Search result 9, run by the STIC search facility, 2016, 2 pages.
Seddon, et al., "Validation of a prediction algorithm for progression to advanced macular degeneration subtypes." JAMA Ophthalmol. 2013; 131(4): 448-455.
Shaaban, Salam A., et al. "Transgenic mice expressing a functional human photopigment." Investigative Ophthalmology & Visual Science (1998); 39.6: 1036-1043.
Shah et al., "Outcomes and risk factors associated with endophthalmitis after intravitreal injection of anti-vascular endothelial growth factor agents." Jefferson Digital Commons. 2011; pp. 1-14.
Shapley, Robert. "Specificity of cone connections in the retina and color vision. Focus on "specificity of cone inputs to macaque retinal ganglion cells"." Journal of Neurophysiology (2006); 95.2: 587-588.
Sheridan, C., "Gene therapy finds its niche." Nat Biotechnol. 2011; 29(2): 121-128.
Shiose, et al., "Gene transfer of a soluble receptor of VEGF inhibits the growth of experimental eyelid malignant melanoma" Invest Ophthalmol Vis Sci. 2000; 41(9): 2395-2403.
Shoji and Nakashima, "Current Status of Delivery Systems to Improve Target Efficacy of Oligonu-cleotides", Current Pharmaceutical Design. (2004); 10(7): 785-796.
Silva, et al., "Age-related macular degeneration and risk factors for the development of choroidal neovascularisation in the fellow eye: a 3-year follow-up study." Ophthalmologica. 2011; 226(3): 110-118.
Simonelli, et al., "Gene therapy for Leber's congenital amaurosis is safe and effective through 1.5 years after vector administration." Mol Ther. 2010; 18(3): 643-650.
Sramek, C. et al., "Non-damaging retinal phototherapy: Dynamic range of heat shock protein expression." Investigative Ophthalmology & Visual Science. 2011; 52(3):1780-1787.
Stefansson, et al., "Metabolic physiology in age related macular degeneration." Prog Retin Eye Res. 2011; 30(1): 72-80.
Stellmach, et al., "Prevention of ischemia-induced retinopathy by the natural ocular antiangiogenic agent pigment epithelium-derived factor." Proc Natl Acad Sci USA. 2001; 98(5): 2593-2597.
Stieger, et al., "In vivo gene regulation using tetracycline- regulatable systems." Advanced Drug Delivery Reviews. 2009; 61(7-8): 527-41.
Stout, et al., "Surgical approaches to gene and stem cell therapy for retinal disease." Hum Gene Ther. 2011; 22(5): 531-535.
Stratford-Perricaudet, et al., "Widespread long-term gene transfer to mouse skeletal muscles and heart." J Clin Invest. 1992; 90(2): 626-630.
Streilein, et al., "Immunobiology and privilege of neuronal retina and pigment epithelium transplants." Vision Res. 2002; 42(4): 487-495.
Sutter, Erich E. "The fast m-transform: a fast computation of cross-correlations with binary m-sequences." SIAM Journal on Computing (1991); 20.4: 686-694.

(56) References Cited

OTHER PUBLICATIONS

Swanson, William H., et al. "Temporal modulation sensitivity and pulse-detection thresholds for chromatic and luminance perturbations." JOSA A (1987); 4.10: 1992-2005.
Szewczenko-Pawlikowski, et al., "Heat shock-regulated expression of calreticulin in retinal pigment epithelium." Mol Cell Biochem. 1997; 177(1-2): 145-52.
Takayama, et al., "Suppression of tumor angiogenesis and growth by gene transfer of a soluble form of vascular endothelial growth factor receptor into a remote organ." Cancer Res. 2000; 60(8): 2169-2177.
Tolentino, et al., "Vascular endothelial growth factor is sufficient to produce iris neovascularization and neovascular glaucoma in a nonhuman primate." Arch Ophthalmol. 1996; 114(8): 964-670.
Ueyama, Hisao, et al. "Analysis of introns and promoters of L/M visual pigment genes in relation to deutan color-vision deficiency with an array of normal gene orders." Journal of Human Genetics (2009); 54.9: 525-530.
Urabe, et al., "Insect cells as a factory to produce adena-associated virus type 2 vectors." Hum Gene Ther. 2002; 13(16): 1935-1943.
US National Health Institute: "Safety and Efficacy Study of rAAV. sFlt-1 in Patients With Exudative Age-Related Macular Degeneration", NCT01494805, Clinical Trials, Updated Dec. 16, 2011; XP002751808, Retrieved from the Internet: URL:https:jjclinicaltrials. govjarchivejNCT01494805/2011_12_16 [retrieved on Dec. 4, 2015].
US National Institute of Health: "Safety and Tolerability Study of AAV2-sFLT01 in Patients With Neovascular Age-Related Macular Degeneration (AMD)", NCT01024998, Clinical Trials, Updated Apr. 13, 2012; XP002751809, Retrieved from the Internet: URL:https:jjclinicaltrials.govjarchive/NCT01024998/2012_04_13 [retrieved on Dec. 4, 2015].
Verma and Somia, "Gene therapy—promises, problems and prospects", Nature 1997; 389: 239-242.
Viard, et al., "Clusterin gene expression mediates resistance to apoptotic cell death induced by heat shock and oxidative stress." J Invest Dermatol. 1999; 112(3): 290-296.
Vigna, et al., "Lentiviral vectors: excellent tools for experimental gene transfer and promising candidates for gene therapy." J Gene Med. 2000; 2(5): 308-316.
Wada, et al., "Expression of vascular endothelial growth factor and its receptor (KDR/flk-1) mRNA in experimental choroidal neovascularization." Curr Eye Res. 1999; 18(3): 203-213.
Wang, et al., "A locus control region adjacent to the human red and green visual pigment genes." Neuron. 1992; 9(3): 429-440.
Wang, et al., "Spatiotemporal control of gene expression by a light-switchable transgene system." Nature Methods. 2012; 9(3): 266-269.
Wells, et al., "Levels of vascular endothelial growth factor are elevated in the vitreous of patients with subretinal neovascularisation." Br J Ophthalmol. 1996; 80(4): 363-366.
Wenkel, et al., "Analysis of immune deviation elicited by antigens injected into the subretinal space." Invest Ophthalmol Vis Sci. 1998; 39(10): 1823-1834.
Wenkel, et al., "Evidence that retinal pigment epithelium functions as an immune-privileged tissue." Invest Ophthalmol Vis Sci. 2000; 41(11): 3467-73.
Wiesel, Torsten N., and Hubel, David H. "Single-cell responses in striate cortex of kittens deprived of vision in one eye." J Neurophysiol (1963); 26.6: 1003-1017.
Wiesmann, et al., "Crystal structure at 1.7 A resolution of VEGF in complex with domain 2 of the Flt-1 receptor." Cell. 1997; 91(5): 695-704.
Wolf, et al., "Preeclampsia and future cardiovascular disease: potential role of altered angiogenesis and insulin resistance." J Clin Endocrinol Metab. 2004; 89(12): 6239-6243.
Wong, et al., "Intravitreal VEGF and bFGF produce florid retinal neovascularization and hemorrhage in the rabbit." Curr Eye Res. 2001; 22(2): 140-147.
Wu, et al., "Self-complementary recombinant adeno-associated viral vectors: packaging capacity and the role of rep proteins in vector purity." Hum Gene Ther. 2007; 18(2): 171-182.
Wulff, et al., "Luteal angiogenesis: prevention and intervention by treatment with vascular endothelial growth factor trap(A40)." J Clin Endocrinol Metab. 2001; 86(7): 3377-3386.
Wykoff, et al., "Perioperative management of patients with reproted povidone-iodine or penicillin/cephalosporin allergies." Presented at the Annual Meeting for the Association for Research in Vision and Opthalmology. Fort Lauderdale, Fl. May 5, 2011; Abstract No. 6416/D880.
Xiao, et al., "Production of high-titer recombinant adena-associated virus vectors in the absence of helper adenovirus." J. Virol. 1998; 72(3): 2224-2232.
Yang, et al., "Cellular and humoral immune responses to viral antigens create barriers to lung-directed gene therapy with recombinant adenoviruses." J Virol. 1995; 69(4): 2004-2015.
Ye, et al., "sFlt-1 gene therapy of follicular thyroid carcinoma." Endocrinology. 2004; 145(2): 817-822.
Ye, Guo-jie, et al. "Development and Evaluation of Cone-Specific Promoters in Non-human Primates for Gene Therapy of Congenital Cone Diseases Including Achromatopsia." Investigative Ophthalmology & Visual Science (2014); 55.13: 837-837.
Yero, et al. "Immunization of mice with Neisseria meningitides serogroup B genomic expression libraries elicits functional antibodies and reduces the level of bacteremia in an infant rat infection model", Vaccine (2005); 23(7): 932-939.
Yin, et al., "Intravitreal injection of AAV2 transduces macaque inner retina." Invest Ophthalmol Vis Sci. 2011; 52(5): 2775-83.
Zhang, et al. "AAV-mediated Gene Therapy Restores Cone Function in a Rat With an M-cone Opsin Deficiency, A Model for Blue Cone Monochromacy", Investigative Opthamology & Visual Science (2011); ARVO Annual Meeting Abstract, 52:1403.
Zhang, et al., "Suppression of tumor growth by oncolytic adenovirus-mediated delivery of an antiangiogenic gene, soluble Flt-1." Mol Ther. 2005; 11(4): 553-562.
Zheng, et al., "Genomic integration and gene expression by a modified adenoviral vector." Nat Biotechnol. 2000; 18(2): 176-180.
Adachi, et al., "A New Recombinant Adena-Associated Virus (AAV)-Based Random Peptide Display Library System: Infection-Defective AAV 1 .9-3 As a Novel Targeted Platform for Vector Evolution"; Gene Therapy and Regulation; vol. 5, No. 1, pp. 31-55 (Oct. 2010).
Adachi, et al., "Drawing a high-resolution functional map of adeno-associated virus capsid by massively parallel sequencing." Nat Commun. (Jan. 2014); 5(1): 3075.
Asuri, et al., "Directed evolution of adeno-associated virus for enhanced gene delivery and gene targeting in human pluripotent stem cells." Mol Ther. (Feb. 2012); 20(2): 329-338. Epub Nov. 22, 2011.
Balakrishnan and Jayandharan, "Basic biology of adeno-associated virus (AAV) vectors used in gene therapy." Curr Gene Ther. (2014); 14(2): 86-100.
Bartel, et al., "Enhancing the Clinical Potential of AAV Vectors by Capsid Engineering to Evade Pre-Existing Immunity." Front Microbiol. (Oct. 4, 2011); 2:204. eCollection 2011.
Dalkara, et al., "Developing Photoreceptor Targeted AAV Variant by Directed Evolution." ARVO Annual Meetinq Abstract Search and Program Planner; vol. 2011, pp. 4381 (May 2011 ).
European Patent Application No. 16880093.6, Extended European Search Report dated May 27, 2019, 10 pages.
Gray, et al., "Directed Evolution of a Novel Adeno-associated Virus (AAV) Vector That Crosses the Seizure-compromised Blood-Brain Barrier (BBB)." Molecular Therapy; vol. 18, No. 3, pp. 570-578 (2010).
Grimm, et al., "In Vitro and In Vivo Gene Therapy Vector Evolution via Multispecies Interbreeding and Retargeting of Adeno-Associated Viruses." Journal of Virology; vol. 82, No. 12, pp. 5887-5911 (Jun. 2008).
Hirsch, et al., "Directed Evolution of the AAV Capsid for Human Embryonic Stem Cell Transduction." Molecular Therapy; vol. 17, Supp. 1, S177-S178 (May 2009).

(56) References Cited

OTHER PUBLICATIONS

International Preliminary Report on Patentability for International Application No. PCT/US2016/068312, dated Jun. 26, 2018, 12 pages.

Invitation to Pay Additional Fees for International Application No. PCT/US2016/068312, dated Feb. 24, 2017, 2 pages.

Jang, et al., "An evolved adeno-associated viral variant enhances gene delivery and gene targeting in neural stem cells." Mol Ther. (Apr. 2011); 19(4): 667-675.

Klimczak; "Molecular Evolution of Adena-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 117 pages (2010).

Koerber, et al., "Molecular evolution of adeno-associated virus for enhanced glial gene delivery." Molecular Therapy (2009); vol. 17, No. 12, pp. 2088-2095.

Kotterman and Schaffer, "Engineering adeno-associated viruses for clinical gene therapy." Nat Rev Genet. (Jul. 2014); 15(7): 445-451. Epub May 20, 2014.

Li, et al., "Engineering and Selection of Shuffled AAV Genomes: A New Strategy for Producing Targeted Biological Nanoparticles." Molecular Therapy; vol. 15, No. 7, pp. 1252-1260 (Jul. 2008).

Li, et al., "Generation of novel AAV variants by directed evolution for improved CFTR delivery to human ciliated airway epithelium." Molecular Therapy (2009), vol. 17, No. 12, pp. 2067-2077.

Lochrie, et al., "Mutations on the External Surfaces of Adena-Associated Virus Type 2 Capsids That Affect Transduction and Neutralization" Journal of Virology (Jan. 2006); 80(2): 821-834.

Maguire, et al., "Directed evolution of adeno-associated virus for glioma cell transduction." J. Neurooncol.; vol. 96, pp. 337-347 (2010).

Michelfelder, et al., "Vectors selected from adeno-associated viral display peptide libraries for leukemia cell-targeted cytotoxic gene therapy." Experimental Hematology; vol. 35, pp. 1766-1776 (2007).

Nonnenmacher, et al., "High capsid-genome correlation facilitates creation of AAV libraries for directed evolution." Mol Ther. (Apr. 2015); 23(4): 675-682. Epub Jan. 14, 2015.

Perabo, et al., "In Vitro Selection of Viral Vectors with Modified Tropism: The Adena-associated Virus Display." Molecular Therapy; vol. 8, No. 1, pp. 151-157 (Jul. 2003).

Perabo, et al., "Combinatorial engineering of a gene therapy vector: directed evolution of adeno-associated virus." The Journal of Gene Medicine (2006); vol. 8, pp. 155-162.

Schaffer, et al.; "Directed evolution of AAV vector mutants for enhanced gene delivery"; Abstracts of Papers American Chemical Society; vol. 227, Part 1, Abstract 172, p. U214 (Mar. 28-Apr. 1, 2004), 2 pages.

Yang, et al., "Directed Evolution of Adeno=Associated Virus (AAV) as Vector for Muscle Gene Therapy." Methods in Molecular Biology; vol. 709, pp. 127-139 (2011).

Yang, et al., "A myocardium tropic adeno-associated virus (AAV) evolved by DNA shuffling and in vivo selection." PNAS; vol. 106, No. 10, pp. 3946-3951 (Mar. 10, 2009).

Zhao, et al., "Molecular evolution by staggered extension process (StEP) in vitro recombination." Nat Biotechnol; vol. 16, No. 3, pp. 258-261 (Mar. 1998).

MUTANT VIRAL CAPSID LIBRARIES AND RELATED SYSTEMS AND METHODS

CROSS REFERENCE TO RELATED APPLICATIONS

This application claims the benefit of U.S. Provisional Application Ser. No. 62/387,177, filed Dec. 23, 2015, the full disclosure of which is herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_008_01US_ST25.txt. The text file is 2 KB, was created on Dec. 21, 2016, and is being submitted electronically via EFS-Web.

FIELD OF THE INVENTION

Embodiments of the present disclosure relate to mutant viral capsid cell libraries, particularly for mutant AAV capsids, individual cells of such libraries, systems and methods for generating the cell libraries, and methods of use thereof to screen for mutant viral capsids with desired characteristics.

BACKGROUND

A promising approach to treating and preventing genetic diseases and disorders is delivery of therapeutic agents with a gene therapy vector such as a viral vector. Illustrative examples of viral vectors suitable for gene therapy include but are not limited to retroviral vectors, lentiviral vectors, adenovirus vectors, herpes virus vectors, alphaviruses vectors, and adeno-associated virus (AAV) vectors. AAV is a 4.7 kb, single stranded DNA virus. Recombinant vectors based on AAV are associated with excellent clinical safety, since wild-type AAV is nonpathogenic and has no etiologic association with any known diseases. In addition, AAV offers the capability for highly efficient gene delivery and sustained transgene expression in numerous tissues, including eye, muscle, lung, and brain. Furthermore, AAV has shown promise in human clinical trials. One example is Leber's congenital amaurosis in which patients treated with a therapeutic delivered by a single subretinal administration of an rAAV vector have experienced sustained clinical benefit from expression of the therapeutic agent for more than four years from the initial date of treatment.

Certain challenges that remain with regard to the design of viral vectors for use in gene therapy include optimizing viral cell tropism and reducing anti-viral or neutralizing host antibody responses. For certain viral vectors, such as AAV, cell tropism and neutralizing antibody responses result largely from the structure of the viral capsid protein. Thus, there is a need in the art for improved tools to screen for mutant viral capsids with desired properties. The present invention addresses these and other issues.

BRIEF SUMMARY OF THE INVENTION

Some embodiments of the present invention include an isolated cell, comprising a heterologous polynucleotide having a coding sequence that encodes a non-naturally occurring mutant viral capsid, wherein the coding sequence for the capsid is operably linked to a promoter on the heterologous polynucleotide, and wherein the heterologous polynucleotide is integrated into the genome of the cell. In one aspect, the heterologous polynucleotide is integrated into the genome of the cell at a pseudo attP site in the cellular genome. In one form, the isolated cell does not encode more than one mutant viral capsid. In one form, the isolated cell comprises one but no more than one heterologous polynucleotide having a coding sequence that encodes a non-naturally occurring mutant viral capsid. That is, an isolated cell of this disclosure preferably does not contain more than one integrated mutant viral capsid gene or coding sequence.

In one embodiment, the heterologous polynucleotide is integrated into the genome of the isolated cell at a pseudo attP site in the cellular genome and there are no other capsid-encoding heterologous polynucleotides integrated into the genome of the cell, such that the isolated cell encodes a single structurally distinct mutant capsid. Accordingly, the mutant viral capsids produced by the isolated cell are structurally identical. That is, the mutant capsids produced by the isolated cell do not comprise a mixture of two or more different mutant capsids. In some forms of the invention, only a single heterologous polynucleotide is integrated into the cell and the polynucleotide is integrated into the cellular genome at a pseudo attP site. In a further aspect, the heterologous polynucleotide further comprises inverted terminal repeats (ITRs).

In some embodiments, the heterologous polynucleotide further comprises a coding sequence encoding a reporter protein, wherein the coding sequence for the reporter protein is operably linked to a promoter. In an illustrative form of the heterologous polynucleotide, ITRs flank the section of the polynucleotide (e.g., the expression cassette on the polynucleotide) comprising the coding sequences for the mutant viral capsid and reporter gene and the promoters to which each coding sequence is operably linked. Furthermore, the heterologous polynucleotide can also comprise a coding sequence encoding a drug-resistance gene, wherein the coding sequence is operably linked to a promoter. Because it is contained on the heterologous polynucleotide, the coding sequence for the drug resistance gene is also integrated into the genome of the cell, and in more specific forms is integrated into a pseudo attP site of the cell. In exemplary forms of the invention, the coding sequence for the drug resistance gene is not flanked by ITRs and is located outside the ITRs that flank the coding sequences for the mutant viral capsid and the reporter protein.

Some embodiments of the present invention include isolated cells, comprising a heterologous polynucleotide that encodes a non-naturally-occurring mutant viral capsid which is operably linked to a promoter and is flanked by Inverted Terminal Repeats (ITRs), wherein the heterologous polynucleotide is integrated into the genome of the cell. In some embodiments the heterologous polynucleotide is flanked by hybrid integrase-specific DNA attachment sites.

In some embodiments, the isolated cell is a eukaryotic cell. In some embodiments, the eukaryotic cell is a mammalian cell or an insect cell. In specific embodiments, the mammalian cell is a HEK-293 cell, HEK-293T cell, or a HeLa cell. In some embodiments, the insect cell is selected from SF9 cells, sf21 cells, S2 (Schneider 2) cells, BTI-TN-5B1-4 cells, and Tni cells.

In some embodiments, the mutant viral capsid is a mutant AAV capsid.

In certain embodiments, the hybrid integrase-specific DNA attachment sites are attR and attL.

In some embodiments, the cell has only one integration event of a heterologous polynucleotide that encodes a non-naturally-occurring mutant viral capsid.

In particular embodiments, the cell comprises a heterologous polynucleotide that encodes a reporter protein that is operably linked to a promoter.

In some embodiments, the reporter protein is selected from green fluorescent protein (GFP), yellow fluorescent protein (YFP), red fluorescent protein (GFP), mCherry, mRaspberry, mPlum, mTomato, dsRed, and luciferase.

In some embodiments, the cell comprises a heterologous polynucleotide that encodes a drug-resistance gene which is operably linked to a promoter.

In some embodiments, the drug-resistance gene is selected from pac (puromycin), bsd (blasticidin), neo (G418), hygB (hygromycin B), and Sh ble (zeocin), Sh bla (gentamycin).

Accordingly, in some embodiments the heterologous polynucleotide can further encode a reporter protein and/or a drug-resistance gene. In some embodiments, the heterologous polynucleotide can comprise a coding sequence that encodes a reporter protein and a coding sequence that encodes a drug resistance protein. Each coding sequence is preferably operably linked to a promoter.

In certain embodiments, the mutant viral capsid is a mutant AAV capsid, and the cell comprises (a) a rep-expressing polynucleotide that encodes one or more of Rep78, Rep68, Rep52, and/or Rep40 from AAV, and an Ad-helper polynucleotide.

Also included are libraries of cells, comprising a plurality of isolated cells described herein, wherein the non-naturally-occurring mutant viral capsid of each cell in the library is distinct from the non-naturally occurring mutant viral capsid of substantially all of the other cells of the library. In some embodiments, the mutant viral capsid is a mutant AAV capsid. In some embodiments, substantially all of the plurality of cells have only one integration event of a polynucleotide that encodes a mutant viral capsid.

Some embodiments are directed to a library of cells, comprising a plurality of isolated cells described herein, wherein each cell in the library encodes a single mutant viral capsid. In some forms, substantially all cells in the library, or at least 90% of the cells in the library each encode a single mutant viral capsid. In other words, each cell in a library, substantially all cells in a library, or at least 90% of the cells in the library comprise(s) no more than one mutant viral capsid gene per cell.

Some embodiments, include a library of cells (i.e., a mutant viral capsid cell library) comprising a plurality of isolated cells as described herein, wherein each cell in the library encodes a single structurally distinct mutant viral capsid, or wherein each cell in greater than 50%, 60%, 70%, or 80%, or at least 90% of the cells in the library encodes a single structurally distinct mutant viral capsid. In preferred aspects, the mutant viral capsid is a mutant AAV capsid.

In some aspects, the plurality of isolated cells in the library can comprise, for example, greater than $10^3$, $10^4$, $10^5$, $10^6$ or greater than $10^7$ cells. According to some aspects, the plurality of isolated cells is a plurality of isolated mammalian or insect cells. In more preferred aspects, the mutant viral capsid gene or coding sequence is integrated into the genome of the isolated cell. In a more preferred aspect, the capsid gene is integrated into a single site in the genome, and even more preferably the single site is a pseudo attP site in the cellular genome.

Some embodiments include a mammalian cell library encoding or expressing mutant viral capsids, wherein each cell, or substantially all cells, or at least 90% of the cells in the library comprise(s) a different heterologous polynucleotide that encodes a non☐naturally-occurring mutant viral capsid, wherein the coding sequence for the non-naturally occurring mutant viral capsid is operably linked to a promoter, and wherein the heterologous polynucleotide is integrated into the genome of the cell using an exogenous or non-Rep integrase that integrates at an integrase-specific DNA attachment site that is native to the cell. In one aspect, the coding sequence for the mutant viral capsid and the promoter to which it is linked are flanked by Inverted Terminal Repeats (ITRs). In one aspect, the integrase-specific DNA attachment site that is native to the cell is a pseudo attP site in the cellular genome. Preferably, the heterologous polynucleotide is integrated into one site in the genome, which is a pseudo attP site. In a further aspect, the non-rep integrase is a serine recombinase or a phage integrase, such as, for example, any of those described herein. In a further aspect, the mutant viral capsid is a mutant AAV capsid. The cell library is preferably diverse. That is, the library preferably expresses, and enables the production of a plurality of distinct or unlike mutant viral capsids, which ultimately assemble to form a plurality of distinct virions whose capsids differ from one another.

Also included are cell culture devices, comprising an isolated cell or a library of cells as described herein.

Certain embodiments relate to systems for generating a mutant viral capsid cell library, comprising a system for inserting a plasmid into a native DNA attachment site in the genome of a eukaryotic cell, comprising (a) a vector encoding a mutant viral capsid which is operably linked to a promoter and flanked by Inverted Terminal Repeats (ITRs), and comprising an integrase-specific DNA attachment site which recombines with the native DNA attachment site in the genome of the cell, and (b) a vector encoding an integrase which is operably linked to a promoter, wherein the integrase promotes integration of the vector of (a) into the native DNA attachment site in the genome of the cell.

In some embodiments, the integrase is a serine recombinase. In some embodiments, the serine recombinase is selected from one or more of the phage integrase Bxb1, the phage integrase φC31, the phage integrase TP901-1, the phage integrase R4, the phage integrase φFC1, the resolvase Tn3, the resolvase γδ, and the invertase Gin.

In certain embodiments, the integrase is a tyrosine recombinase. In some embodiments, the tyrosine recombinase is selected from one or more of lambda integrase, HK022 integrase, P22 integrase, HP1 integrase, L5 integrase, Cre recombinase, FLP invertase, and XerC.

In some embodiments, the native DNA attachment site is a pseudo attP site in the genome of the eukaryotic cell, the integrase-specific DNA attachment site is φC31 attB, and the integrase is φC31.

In some embodiments, the native DNA attachment site is a pseudo attP site, the integrase-specific attachment site is Bxb1 attB, and the integrase is Bxb1.

Certain systems comprise a plurality of eukaryotic cells, which comprise the native DNA attachment site in the genome of the cells.

In some embodiments, the vector of (a) further encodes a reporter protein which is in between the ITRs. In some embodiments, the vector of (a) further encodes a drug resistance gene which is outside of the ITRs. In some embodiments the vector of (a) encodes a mutant viral capsid, a reporter protein, and a drug resistance gene. The coding sequence for the mutant viral capsid is operably linked to a promoter on the vector of (a).

Also included are systems for generating a mutant viral capsid cell library, comprising (a) a system for introducing a first integrase-specific DNA attachment site into the genome of the eukaryotic cell, comprising (i) a vector comprising the first integrase-specific DNA attachment site and a second integrase-specific DNA attachment site which recombines with a native DNA attachment site in the genome of the cell, and (ii) a vector encoding a first integrase which is operably linked to a promoter, wherein the first integrase promotes integration of the vector of (a)(i) into the genome of the cell via recombination between the second integrase-specific attachment site and the DNA attachment site in the genome of the cell; and (b) a system for inserting a plasmid into the first DNA attachment site in the genome of a eukaryotic cell, comprising (i) a vector encoding a mutant viral capsid which is operably linked to a promoter and flanked by Inverted Terminal Repeats (ITRs), and comprising a third DNA attachment site which recombines with the first DNA attachment site, and (ii) a vector encoding a second integrase which is operably linked to a promoter, wherein the second integrase promotes integration of the vector of (b)(i) into the first DNA attachment site.

In some embodiments, the first and/or second integrase is a serine recombinase. In some embodiments, the serine recombinase is selected from one or more of the phage integrase Bxb1, the phage integrase φC31, the phage integrase TP901-1, the phage integrase R4, the phage integrase φFC1, the resolvase Tn3, the resolvase γδ, and the invertase Gin. In some embodiments, the first and/or second integrase is a tyrosine recombinase. In some embodiments, the tyrosine recombinase is selected from one or more of lambda integrase, HK022 integrase, P22 integrase, HP1 integrase, L5 integrase, Cre recombinase, FLP invertase, and XerC.

In certain embodiments of the system of (a), the first integrase-specific DNA attachment site is Bxb1 attP, the second integrase-specific attachment site is φC31 attB, and the first integrase is φC31. In some embodiments of the system of (b), the third DNA attachment site is Bxb1 attB, and the second integrase is Bxb1.

Certain systems comprises a plurality of eukaryotic cells, which comprise the native DNA attachment site in the genome of the cell that recombines with the second integrase-specific DNA attachment site.

In some embodiments, the vector of (a)(i) and (a)(ii) are on separate vectors. In some embodiments, the vector of (b)(i) and (b)(ii) are on separate vectors.

In some embodiments, the vector of (b)(i) encodes a reporter protein which is in between the ITRs. In some embodiments, the vector of (b)(i) encodes a drug resistance gene which is outside of the ITRs.

Also included are kits that comprise an isolated cell, library of cells, or system described herein.

Particular embodiments relate to methods for generating a mutant viral capsid cell library, comprising (a) transfecting a plurality of eukaryotic cells with a first and a second vector, wherein the plurality of cells comprise an integrase-specific DNA attachment site in their genome, wherein the first vector encodes a mutant viral capsid which is operably linked to a promoter which is flanked by Inverted Terminal Repeats (ITRs) and comprises an integrase-specific DNA attachment site that recombines with the integrase-specific DNA attachment site in the cell, and wherein the second vector encodes a heterologous integrase which promotes integration at the DNA attachment site, and (b) selecting the plurality of cells for expression of the vector, thereby generating the mutant viral capsid cell library.

In some embodiments, the integrase-specific DNA attachment site in the genome of the cells is a single non-native Bxb1 attP site, the integrase is Bxb1, and the integrase-specific DNA attachment site in the vector is Bxb1 attB. In some embodiments, the integrase-specific DNA attachment site in the genome of the cells is a single non-native φC31 attP site, the integrase is φC31, and the integrase-specific DNA attachment site in the vector is φC31 attB.

In some embodiments, substantially all of the selected cells have only one integration event of the vector which is at the single non-native attP site.

In some embodiments, the integrase-specific DNA attachment site in the genome of the cell is a native pseudo attP site, the integrase is φC31, and the integrase-specific DNA attachment site in the vector is φC31 attB. Some embodiments include transfecting a titrated molar ratio of the first vector:second vector, wherein substantially all of the selected cells have only one integration event of the vector at a pseudo native attP site.

In some embodiments, the vector that encodes the mutant viral capsid further encodes a reporter protein, optionally green fluorescent protein (GFP).

In some embodiments, the mutant viral capsid is a mutant AAV capsid.

Certain embodiments include transfecting the mutant AAV capsid cell library with an AAV rep-expressing polynucleotide that encodes one or more of Rep78, Rep68, Rep52, and/or Rep40, and/or a helper vector, and incubating the cell library for a time sufficient to produce virions that comprise the mutant AAV capsid.

Some embodiments include contacting the cells with a helper virus encoding a rep protein, and incubating the cell library for a time sufficient to produce virions that comprise the mutant AAV capsid. In some embodiments, the helper virus is an adenovirus or a herpes virus.

Particular embodiments include collecting and screening the virions for at least one phenotype relative to a wild-type AAV capsid, wherein the at least one phenotype is altered cell tropism, reduced neutralizing antibody binding, or both. In some embodiments, the screening comprises infecting target cells with the virions under suitable conditions and isolating the infected cells.

Some embodiments include collecting and screening the virions for at least one phenotype, wherein screening comprises infecting target cells with the virions under suitable conditions or administering the virions to a mammalian subject, followed by isolating the infected target cells or isolating a target tissue from the mammalian subject.

In particular embodiments, the step of isolating the infected cells is based on expression of a reporter protein encoded by the virions. Examples of reporter proteins include green fluorescent protein (GFP), among others described herein and known in the art.

In some embodiments, the target cells comprise retinal cells and the at least one phenotype is increased tropism towards (or infectivity of) the retinal cells.

In some embodiments, the at least one phenotype is reduced neutralizing antibody binding and the suitable conditions comprise the presence of neutralizing antibodies. In some embodiments, the target cells are HeRC32 cells which express a rep protein.

Certain embodiments include the step of performing reverse transcription polymerase chain reaction (RT-PCR)

on RNA from the infected, isolated cells to identify and sequence a mutant AAV capsid of interest.

In some embodiments, screening comprises administering a library of mutant AAV virions to a mammalian subject and thereafter isolating a tissue or cell sample from the subject, and then evaluating the tissue or cell sample to identify mutant AAV capsid RNA present in the tissue or cell sample. According to some embodiments, identifying mutant AAV capsid RNA comprises performing RT-PCR on RNA from the infected cell, isolated tissue, or cell sample, and then sequencing AAV mutant capsid DNA. Identifying mutant capsid RNA can further comprise the step of transducing the isolated cell or tissue sample with an adenovirus prior to performing RT-PCR. In one embodiment, the adenovirus is Ad5. In one embodiment, mutant AAV virions produced by a cell library of the present invention are screened for altered cell tropisms by injecting the virions into the eye of a mammalian subject and thereafter isolating retinal tissue from the subject. In a more specific aspect, the method comprises injecting the virions into the vitreous of an eye in the subject and then after a period, isolating retinal tissue from the subject.

As indicated above, some embodiments include the step of increasing the quantity of mutant AAV capsid RNA in an infected target cell. This step can occur prior to and in addition to performing RT-PCR. According to some aspects, increasing the quantity of mutant AAV capsid RNA in an infected target cell comprises transducing target cells or target tissue with an adenovirus or a herpes simplex virus. In a specific embodiment the adenovirus is Ad5. In another specific embodiment, the herpes simplex virus is HSV-1.

DETAILED DESCRIPTION OF THE INVENTION

Figure 1A:
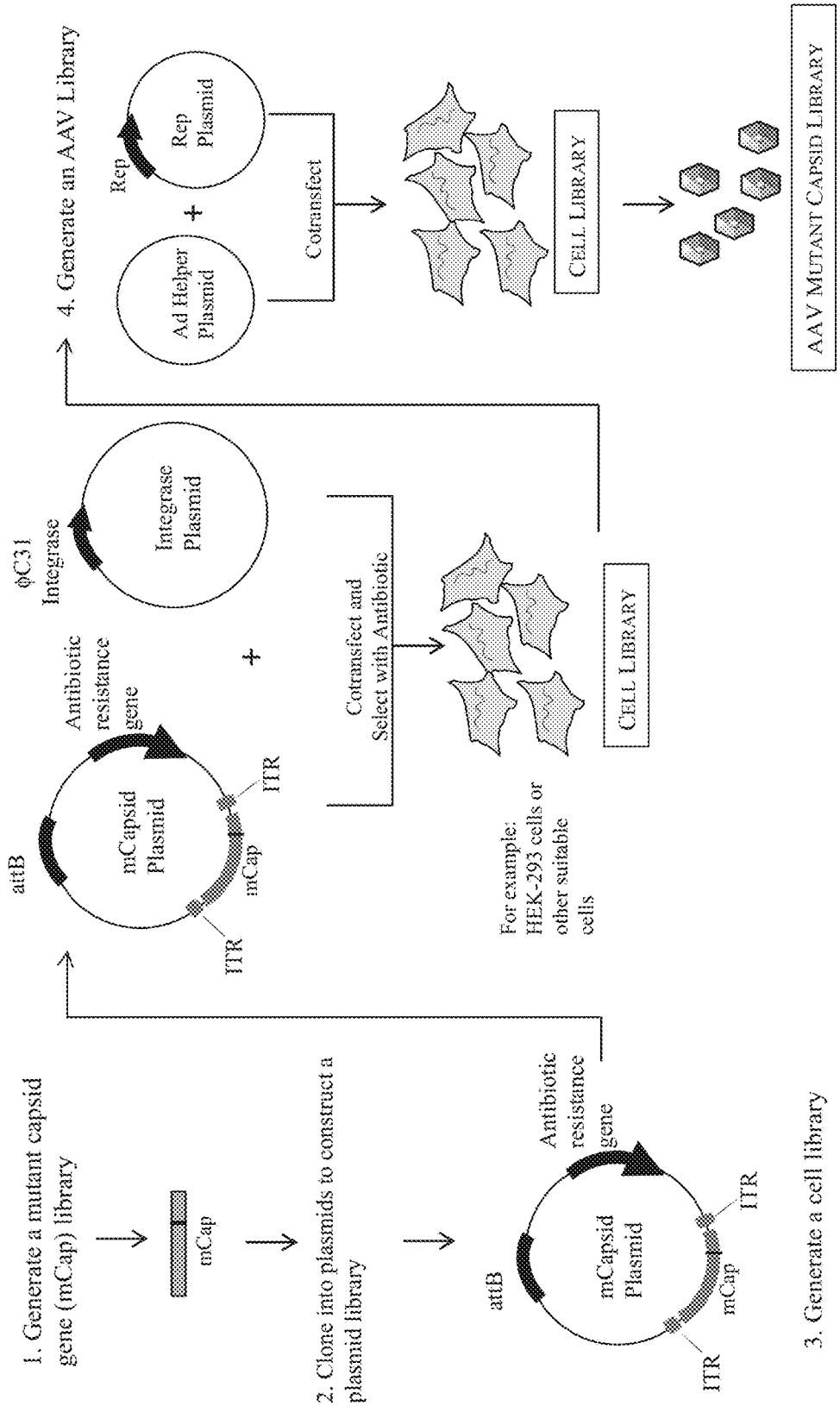
FIGS. 1A and 1B show one illustrative embodiment for producing (FIG. 1A) and screening (FIG. 1B) a mutant viral capsid library according to the present invention.

Embodiments of the present disclosure relate to mutant viral capsid cell libraries, particularly for mutant AAV capsids, individual cells of such libraries, systems and methods for generating the cell libraries, and methods of use thereof to screen for mutant viral capsids with desired characteristics. Such embodiments allow for the generation of viral capsid libraries with high diversity, for example, with up to billions of variants or more and little to no cross-packaging, in the least because all or substantially all of the cells in a given library contain a single integrated copy of their own mutant viral capsid gene.

The cells and libraries can be used, for example, to screen and select for mutant or variant capsids having desired properties relative to wild-type capsids, such as variants with reduced binding to neutralizing antibodies and/or variants with altered cell tropism. In specific instances, the variant capsids, particularly AAV capsids, can be selected for improved retinal cell tropism.

Definitions

The term "retinal cell" refers to any of the cell types that comprise the retina, including but not limited to retinal ganglion cells, amacrine cells, horizontal cells, bipolar cells, and photoreceptor cells, including rods and cones, Müller glial cells, and retinal pigmented epithelium.

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "AAV" is an abbreviation for adeno-associated virus, and may be used to refer to the virus itself or derivatives thereof. The term covers all subtypes and both naturally occurring and recombinant forms, except where required otherwise. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as a "rAAV vector particle" or simply a "rAAV vector". Thus, production of an rAAV particle necessarily includes production of an rAAV vector, as such a vector is contained within a rAAV particle.

The term "replication defective" as used herein relative to an AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

An "AAV variant" or "AAV mutant" as used herein refers to a viral particle composed of a variant AAV capsid protein, where the variant AAV capsid protein comprises at least one amino acid difference (e.g., amino acid substitution, amino acid insertion, amino acid deletion) relative to a corresponding parental AAV capsid protein. In some instances, the variant capsid protein confers reducing binding to host antibodies and/or increased infectivity of a retinal cell compared to the infectivity of the retinal cell by an AAV virion comprising the corresponding parental AAV capsid protein. An AAV variant or mutant AAV virion will preferably contain a polynucleotide encoding the mutant capsid proteins that make up the mutant AAV virion capsid.

The abbreviation "rAAV" refers to recombinant adeno-associated virus, also referred to as a recombinant AAV vector (or "rAAV vector"). A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

As used herein, the term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises an additional, non-coding, sequence. For example, the gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, a "transgene" is a gene that is delivered to a cell by a vector.

As used herein, the term "gene product" refers to the desired expression product of a polynucleotide sequence such as a polypeptide, peptide, protein.

As used herein, the terms "polypeptide," "peptide," and "protein" refer to polymers of amino acids of any length. The terms also encompass an amino acid polymer that has been modified; for example, disulfide bond formation, glycosylation, lipidation, phosphorylation, or conjugation with a labeling component.

The term "polynucleotide" or "nucleic acid" as used herein includes mRNA, RNA, cRNA, cDNA, and DNA. The term typically refers to polymeric form of nucleotides of at least 10 bases in length, either ribonucleotides or deoxyribonucleotides or a modified form of either type of nucleotide. The term includes single and double stranded forms of DNA. The terms "isolated" DNA and polynucleotide and nucleic acid refers to a DNA molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode a polypeptide. Included within the term "polynucleotide" are DNA segments and smaller fragments of such segments, and also recombinant vectors, including, for example, plasmids, cosmids, phagemids, phage, viruses, and the like.

Additional coding or non-coding sequences may, but need not, be present within a polynucleotide. Hence, the polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a mutant viral capsid operably linked to a promoter is an expression cassette that may include other elements in addition to the gene and promoter, e.g. poly-adenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette or polynucleotide "consisting essentially of" a gene encoding a mutant viral capsid operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a mutant viral capsid operably linked to a promoter, and a polyadenylation sequence consists only of the promoter, polynucleotide sequence encoding the mutant viral capsid, and polyadenylation sequence. As another example, a polypeptide "consisting of" a recited sequence contains only the recited sequence.

As used herein, the terms "sequence identity," for example, "% sequence identity," refers to the degree of identity between two or more polynucleotides when aligned using a nucleotide sequence alignment program; or between two or more polypeptide sequences when aligned using an amino acid sequence alignment program. Similarly, the term "identical" or percent "identity" when used herein in the context of two or more nucleotide or amino acid sequences refers to two sequences that are the same or have a specified percentage of amino acid residues or nucleotides when compared and aligned for maximum correspondence, for example as measured using a sequence comparison algorithm, e.g. the Smith-Waterman algorithm, etc., or by visual inspection. For example, the percent identity between two amino acid sequences may be determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. As another example, the percent identity between two nucleotide sequences may be determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

The term "expression" as used herein encompasses the transcription and/or translation of an endogenous gene, a transgene or a coding sequence in a cell.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

An "enhancer" as used herein encompasses a cis-acting element that stimulates transcription of adjacent genes. Enhancers can function (i.e., can be associated with a coding sequence) in either orientation, over distances of up to several kilobase pairs (kb) from the coding sequence and from a position downstream of a transcribed region.

A "termination signal sequence" as used herein encompasses any genetic element that causes RNA polymerase to terminate transcription, such as for example a polyadenylation signal sequence.

A "polyadenylation signal sequence" as used herein encompasses a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, the terms "operatively linked" or "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wild-type virus or cell.

An "endogenous" recognition site refers to a site that is "native" to the genome, or a recognition site that occurs naturally in the genome of a cell (i.e., the sites are not introduced into the genome, for example, by recombinant means).

The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

The term "introducing", as used herein, includes delivery of a vector to a cell or cells, for example, for recombinant protein expression and/or for the introduction of one or more DNA attachment sites. Such a introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

The terms "integrase" or "recombinase" refer to a family of enzymes that mediate site-specific recombination between specific DNA sequences recognized by the recombinase (see, e.g., Esposito and Scocca, Nucleic Acids Res. 25:3605-3614, 1997); Nunes-Duby et al., Nucleic Acids Res. 26:391-406, 1998; and Stark et al., Trends in Genet. 8:432-439, 1992).

A "DNA attachment site" or "integrase-specific DNA attachment site" refers to a stretch, domain or region of nucleotides that, when the system is employed, is recognized by the integrase of the system in which the genome attachment site is a member. "System members" as used herein refer to elements of the systems (i.e., a pair of integration-specific recognition sites and a corresponding integrase) that can interact to accomplish site-specific recombination. Attachment sites may vary in length, but typically ranges from about 20 to about 300 nucleotides in length, or from about 23 to about 100 nucleotides, or from about 28 to about 50 nucleotides in length, and generally about 40 nucleotides in length. Attachment sites can be in the genome of a cell, or in a vector. A DNA attachment site in the genome of a cell can be a "native" or "endogenous" DNA attachment site, which occurs naturally in the cell, or an "exogenous," "non-native," "engineered," or "introduced" attachment site, which has been introduced into the genome of the cell by recombinant techniques.

A "pseudo site" or "pseudo DNA attachment site" refers to a DNA sequence comprising a recognition site that is bound by a recombinase enzyme where the recognition site differs in one or more nucleotides from a wild-type recombinase recognition sequence and/or is present as an endogenous sequence in a genome that differs from the sequence of a genome where the wild-type recognition sequence for the recombinase resides. In some embodiments a "pseudo attP site" or "pseudo attB site" refer to pseudo sites that are similar to the recognitions site for wild-type phage (attP) or bacterial (attB) attachment site sequences, respectively, for phage integrase enzymes, such as the phage φC31 or Bxb1. In some embodiments, the pseudo attP site is present in the genome of a host cell, while the pseudo attB site is present on a targeting vector in the system of the invention. A "pseudo att site" is a general term that can refer to a pseudo attP site or a pseudo attB site. It is understood that att sites or pseudo att sites may be present on linear or circular nucleic acid molecules.

The term "modulating" includes "increasing" or "stimulating," as well as "decreasing" or "reducing," typically in a statistically significant or a physiologically significant amount as compared to a control. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the amount produced by no composition or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (or a control composition, including all integers in between.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 90%, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected"; "transfected" or "transformed" dependent on the means used for administration, introduction or insertion of heterologous DNA (i.e., the vector) into the cell. A cell is transduced with exogenous or heterologous DNA when the DNA is introduced into the cell by a virus. A cell is transfected with exogenous or heterologous DNA when the DNA is introduced into the cell by a non-viral method. Non-viral methods include chemical (e.g., lipofection) methods. The terms "transduced" and "infected" are used interchangeably herein to refer to cells that have received a heterologous DNA or heterologous polynucleotide from a virus.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

Unless otherwise indicated, all terms used herein have the same meaning as they would to one skilled in the art and the practice of the present invention will employ, conventional techniques of microbiology and recombinant DNA technology, which are within the knowledge of those of skill of the art.

Cells and Cell Libraries for Screening Mutant Capsids

The present invention provides methods for generating stable cell libraries that can be used to produce a plurality of variant AAV virions (i.e., a mutant AAV library), or more generally a plurality of mutant virions. The mutant AAV library can be tested in vitro and screened in vivo to identify and select virions with unique and useful properties. The variant AAV virions produced by a cell library of this disclosure can comprise a plurality of distinctive mutations in one or more of their capsid protein(s) (VP1, VP2, and/or VP3), which may endow one or more of the virions in the library with an altered and desirable tropism and/or an ability to evade antibodies in an animal subject. This can be important because antibodies having the ability to bind to the AAV capsid may neutralize the ability of a recombinant AAV gene therapy virion to infect a target cell. The tropism, or cellular range, of an adeno-associated virus (AAV) is typically determined by the binding of the AAV capsid to molecules or receptors present on the surface of target cells. The ability to effectively modify the AAV capsid, for example by introducing one or more amino acid substitutions or peptide insertions into a capsid protein, and to then generate a stable cell library that can serve as a stable and renewable source for the continued and on-demand production of these variant AAV virions may be a valuable tool for discovering AAV virions that can infect cells in a target tissue while evading neutralizing antibodies. As such the present invention is expected to have utility in gene therapy research and vector development.

A cell library of the present invention can encode and express a library of variant AAV virions, and more generally a plurality of variant virions, having one or more mutations in their capsid proteins. In addition to the many embodiments contemplated by the present invention, the present invention includes methods for making mutant AAV capsid cell libraries, cell libraries produced by the method, isolated cells contained by the libraries, clonal cell lines that may be derived from a cell library, and the vectors and vector systems used in the method for generating a cell library.

One embodiment is an isolated cell comprising a heterologous polynucleotide having a coding sequence (e.g., a mutant cap gene) that encodes a non-naturally occurring mutant viral capsid, wherein the coding sequence for the capsid is operably linked to a promoter on the polynucleotide, and wherein the heterologous polynucleotide is integrated into the genome of the cell. In preferred embodiments, the isolated cell comprises no more than two heterologous polynucleotides, and most preferably no more than one heterologous polynucleotide encoding a mutant viral capsid integrated into the genome of the cell. Accordingly, an isolated cell of this disclosure will preferably comprise one heterologous polynucleotide encoding a non-naturally occurring mutant viral capsid and the polynucleotide will be integrated into the genome of the cell. In a preferred aspect, the heterologous polynucleotide is integrated into the genome of the isolated cell at a pseudo attP site in the cellular genome. Even more preferably, the heterologous polynucleotide is integrated into the genome of the isolated cell at and only at a pseudo attP site in the cellular genome. In a preferred form, the mutant viral capsid is a mutant AAV capsid. In preferred forms, the coding sequence is operably linked to a heterologous promoter on the polynucleotide and the polynucleotide is integrated at no more than one site or no more than one pseudo attP site in the cellular genome. Stated in other terms, the isolated cell of this invention preferably does not encode or express more than one mutant viral capsid, or in more specific embodiments does not encode more than one mutant AAV capsid. In other words, when the isolated cell is cultured, the mutant viral capsid protein(s) expressed by the cell are structurally identical one to the other, such that a single cell does not express a heterogeneous population of dissimilar capsids encoded by two or more different mutant capsid genes. In some forms, the heterologous polynucleotide is flanked by inverted terminal repeats (ITRs) and the polynucleotide is stably integrated into the genome of the cell. In some forms the polynucleotide further includes a coding sequence for a reporter protein.

In other embodiments, an isolated cell according to this disclosure comprises one heterologous polynucleotide or at most two heterologous polynucleotides. In cases where the cell comprises two heterologous polynucleotides, the two heterologous polynucleotides preferably encode structurally identical mutant viral capsids.

The cell or cell line can be a eukaryotic cell. Exemplary eukaryotic cells include mammalian cells and insect cells. Specific non-limiting examples of useful mammalian and insect cells are described below.

Other embodiments are directed to a library of cells, comprising a plurality of isolated cells described herein, wherein less than 50% of the cells in the library, more preferably less than 10%, and even more preferably less than 5% of the cells in the library encode two or more different mutant viral capsid proteins per cell. In certain embodiments, at least 95% or at least 90% of the cells in the library of cells encode only one mutant viral capsid protein.

Another embodiment is a method for generating a mutant viral capsid cell library, comprising (a) transfecting a plurality of eukaryotic cells with a mixture of first and second plasmids or vectors, wherein the plurality of cells comprise an integrase-specific DNA attachment site in their genome, wherein the first plasmid or vector contains an integrase-specific DNA attachment site and a coding sequence that encodes a non-naturally occurring mutant viral capsid, wherein the integrase-specific DNA attachment site in the first plasmid or vector recombines with a pseudo attP site in the cellular genome, wherein the coding sequence for the mutant viral capsid protein is operably linked to a promoter on the first plasmid or vector, wherein the second plasmid or vector encodes an integrase, which promotes recombination and thereby integration of the first plasmid or vector into the genome of the cell at a pseudo attP site, and wherein the ratio (e.g., the molar ratio) of first plasmid to second plasmid in the mixture is such that in greater than 70%, 80%, 90%, or greater than 95% of the cells in the population exposed to the mixture of plasmids or transfected by the plasmids, no more than one plasmid or vector encoding a mutant viral capsid is integrated per cell, and (b) selecting the population of cells from step (a) for expression of the first plasmid or vector, thereby generating a mutant viral capsid cell library. In some embodiments the ratio (e.g., molar ratio) of the first:second plasmids or vectors in the mixture is about 1:200, 1:100, 1:50, 1:40, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, or 1:2. In a preferred embodiment, the molar ratio of the first:second plasmids or vectors is about 1:50.

In some embodiments the ratio (e.g., molar ratio) of the plasmid encoding the mutant viral capsid plasmid to the plasmid encoding the integrase in the mixture is at least 1:10, 1:20, 1:30, 1:40, 1:50, or 1:100. In some aspects, the integrase is an exogenous or non-Rep integrase. In some aspects, the exogenous or non-Rep integrase is a phage integrase.

In preferred forms of the method described above for generating a mutant viral capsid cell library, the percentage of cells in a population receiving two or more mutant viral capsid genes or coding sequences following transfection with the first and second plasmids is less than 10%. Put in other terms, the percentage of cells integrating two or more capsid genes is less than 10% and even more preferably less than about 5%.

In some forms of this method greater than 35%, greater than about 40%, greater than 60%, and most preferably greater than 70% of the cells in the population (i.e., in the plurality of cells) are transfected by the first plasmid at step (a). That is, the transfection efficiency of the method is preferably at least 35%, 40%, 50%, 60%, or is at least 70%.

In specific forms of the method for generating a mutant viral capsid cell library, the non-naturally occurring mutant viral capsid is a non-naturally occurring mutant AAV capsid, and the integrase-specific DNA attachment site is a φC31 integrase-specific attB attachment site, the integrase of the second plasmid is φC31, and the polynucleotide sequence containing the mutant cap gene is integrated into the cellular genome at a pseudo attP site in the cellular genome.

In a further form, the heterologous polynucleotide is stably integrated into the cellular genome at a pseudo attP site in the cellular genome. According to preferred forms of the method, the rate or frequency of multiple (two or more) integration events per cell (i.e., the integration of two or more mutant cap genes per cell) in the population of cells or cell library is such that less than 10% of the cells, or more preferably less than 5% of the cells in the library integrate more than one mutant capsid gene per cell. In certain embodiments, at least 95% or at least 90% of the cells in the population of cells or cell library comprise only one stably integrated heterologous polynucleotide.

The invention further encompasses methods for screening mutant AAV virions for at least one phenotype relative to a wild-type or naturally occurring AAV capsid. In some embodiments, the at least one phenotype is altered cell tropism, reduced neutralizing antibody binding, or both altered cell tropism and reduced neutralizing antibody binding relative to the corresponding parental or relative to a naturally occurring AAV capsid. In one embodiment, the method comprises contacting target cells or a target tissue with a mutant AAV virion library, isolating the target cells or tissue, performing reverse transcription polymerase chain reaction (RT-PCR) on RNA from the isolated target cells or tissue to convert mutant AAV capsid RNA present in the isolated cells or tissue to cDNA, and sequencing mutant capsid DNA, thereby identifying mutant AAV virions that successfully infected the target cells or cells in the target tissue. The method can optionally further comprise contacting the isolated target cells or tissue with adenovirus prior to performing RT-PCR. By target cells and tissues is meant the intended targets of a gene therapy protocol. For purposes of screening a mutant virion library in vivo, such as a mutant AAV capsid library, target cells and tissues can be tested or screened as described above to determine whether they were infected by a mutant AAV virion. Mutant virions that productively infect cells within a target tissue may be candidates for further rounds of selection and study as potential gene therapy vectors for the delivery of a therapeutic gene to target cells in need of therapy.

Certain embodiments relate to isolated cells and cell lines that comprise at least one integrated, non-naturally-occurring mutant (variant) viral capsid, including viral packaging cell lines that comprise only one integrated mutant viral capsid, and libraries of the cells/cell lines. Among other advantages, such embodiments can reduce or prevent cross-packaging of different mutant viral capsids by ensuring the generation of viruses with only one type of mutant viral capsid from each cell (or cell line), and thereby optimizing the rescue of selected or desired mutants during directed evolution and screening processes.

Exemplary isolated cells or cell lines comprise a heterologous polynucleotide that encodes a non-naturally-occurring mutant viral capsid which is operably linked to a promoter and is flanked by Inverted Terminal Repeats (ITRs), wherein the heterologous polynucleotide is integrated into the genome of the cell and is flanked by hybrid integrase-specific DNA attachment sites.

In certain embodiments, the cell or cell line is a eukaryotic cell. Exemplary eukaryotic cells include mammalian cells and insect cells.

Examples of useful mammalian cells include human embryonic kidney cell lines (HEK-293 cells, HEK-293T cells, 293 cells sub-cloned for growth in suspension culture, see, e.g., Yuan et al., Hum Gen Ther. 22:613-24, 2011; Graham et al., J. Gen Virol. 36:59 (1977)); human cervical carcinoma cells (HELA, ATCC CCL 2); monkey kidney CV1 line transformed by SV40 (COS-7, ATCC CRL 1651); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NS0 and Sp2/0. In specific embodiments, the cell is a HEK-293 cell or a derivative thereof.

Examples of useful insect cell lines include SF9 cells, sf21 cells, S2 (Schneider 2) cells, BTI-TN-5B1-4 (High Five™ Cells), and Tni cells (see, e.g., Drugmand et al., Biotechnology Adv. 30:1140-57, 2011; and Murphy and Piwnica□Worms, Curr Protoc Protein Sci. Chapter 5: Unit 5.4, 2001). In specific embodiments, the insect cell is an SF9 cell or a derivative thereof.

Non-limiting examples of useful promoters include the SV40, CMV, and elongation factor (EF)-1 promoters, among others.

Non-naturally-occurring mutant (variant) viral capsids can be derived from any viral capsid. Examples include adeno-associated virus (AAV), alphavirus, adenovirus, herpes virus, and retrovirus capsids, including capsids from Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)), and lentiviruses such as HIV (human immunodeficiency virus; including HIV type 1, and HIV type 2), visna-maedi virus (VMV) virus, the caprine arthritis-encephalitis virus (CAEV), equine infectious anemia virus (EIAV), feline immunodeficiency virus (FIV), bovine immune deficiency virus (BIV), and simian immunodeficiency virus (SIV). In particular embodiments, the mutant viral capsid is a mutant AAV capsid. For AAV, the mutant or variant AAV capsid proteins may be derived from any adeno-associated virus serotype, including without limitation, AAV1, AAV2, AAV3, AAV4, AAV5, AAV6, AAV7, AAV8, AAV9, AAV10, etc. Exemplary mutant capsid proteins may be altered by the insertion, deletion or substitution of nucleotides in the VP1, VP2 or VP3 sequence(s), including combinations thereof.

Mutant viral capsids and polynucleotides that encode the same can be generated by any variety of mutagenesis techniques. For example, in certain instances, any number of random mutant viral capsids can be prepared by loop insertion mutagenesis (see, e.g., Heinis and Johnsson, Methods Mol Biol. 634:217-32, 2010) and/or error prone polymerase chain reaction (PCR) (see, e.g., McCullum et al., Methods Mol Biol. 634:103-9, 2010). These can be incorporated into an appropriate vector for introduction into the cells described herein.

By "Inverted Terminal Repeats (ITRs)" including "functional AAV ITR sequences," is meant that the ITR sequences function as intended for the rescue, replication and packaging of the virion, for example, the AAV vector particle. Hence, AAV ITRs for use in the vectors of the invention need not have a wild-type nucleotide sequence, and may be altered by the insertion, deletion or substitution of nucleotides or the AAV ITRs may be derived from any of several AAV serotypes, e.g. AAV1, AAV2, AAV3, AAV4, AAV5, AAV6, AAV7, AAV8, AAV9, AAV10.

In some embodiments, the polynucleotide encoding the mutant viral capsid (which is flanked itself by ITRs) is flanked by hybrid integrase-specific DNA attachment sites, typically two of such attachment sites, one at each of the 5' and 3' ends of the polynucleotide. A "hybrid DNA attachment site" or "hybrid integrase-specific DNA attachment site" refers to a DNA attachment that results from a recombination event between two corresponding DNA attachment sites, and which each comprise part of the two sites. Certain hybrid DNA attachment sites are irreversible and can no longer be the subject of further recombination event. Certain hybrid DNA attachment sites are reversible and can be the subject of a further recombination event. In specific embodiments, the hybrid DNA attachment sites each comprise part of an attP site and part of an attB site. Specific examples of hybrid DNA attachment sites include attR and attL.

In specific embodiments, the isolated cell has only one integration event of a heterologous polynucleotide that encodes a non-naturally-occurring mutant viral capsid (e.g., a single integrated copy of a heterologous polynucleotide that encodes a single mutant viral capsid). In these and related embodiments, the isolated cell comprises or expresses a single mutant or variant viral capsid, for example, a single mutant AAV capsid.

In some embodiments, the isolated cell (or cell line) comprises an exogenous or non-native reporter protein, for instance, a heterologous polynucleotide that encodes a reporter protein that is operably linked to a promoter. Such can be used to identify transfected cells, for example, cells which have been successfully transfected with the heterologous polynucleotide that encodes the mutant viral capsid. In some embodiments, the polynucleotide that encodes the reporter protein is on a separate vector or expression cassette than the polynucleotide that encodes the mutant viral capsid. In particular embodiments, the polynucleotide that encodes the reporter protein is on the same vector or expression system as the polynucleotide that encodes the mutant viral capsid. In some instances, the polynucleotide that encodes the mutant viral capsid and the polynucleotide that encodes the reporter protein are operably linked to the same promoter, and optionally separated by translational regulatory elements such as an internal ribosomal entry site (IRES). In certain instances, the polynucleotide that encodes the mutant viral capsid and the polynucleotide that encodes the reporter protein are operably linked to different promoters, which can be oriented in the same or different direction.

Examples of reporter proteins (and genes) include fluorescent reporter proteins, luminescent reporter proteins, and substrate-specific reporter proteins. Specific examples include green fluorescent protein (GFP), yellow fluorescent protein (YFP), red fluorescent protein (GFP), mCherry, mRaspberry, mPlum, mTomato, dsRed, luciferase, and β-galactosidase (β-gal), among others.

In certain embodiments, the isolated cell (or cell line) comprises an exogenous or non-native drug-resistance protein or gene, for instance, a heterologous polynucleotide that encodes a drug-resistance protein which is operably linked to a promoter. Exemplary drug-resistance proteins or genes include pac (puromycin), bsd (blasticidin), neo (G418), hygB (hygromycin B), Sh ble (zeocin), Sh bla (gentamycin). Such can be used to select for transfected cells, for example, cells which have been successfully transfected with the heterologous polynucleotide that encodes the mutant viral capsid. In some embodiments, the polynucleotide that encodes the drug-resistance protein is on a separate vector or expression cassette than the polynucleotide that encodes the mutant viral capsid. In particular embodiments, the polynucleotide that encodes the drug-resistance protein is on the same vector or expression system as the polynucleotide that encodes the mutant viral capsid. In some instances, the polynucleotide that encodes the mutant viral capsid and the polynucleotide that encodes the drug-resistance protein are operably linked to the same promoter, and optionally separated by translational regulatory elements such as an internal ribosomal entry site (IRES). In certain instances, the polynucleotide that encodes the mutant viral capsid and the polynucleotide that encodes the drug-resistance protein are operably linked to different promoters, which can be oriented in the same or different direction. Such embodiments can also be combined with reporter proteins, as described herein. For instance, where the cell comprises a polynucleotide that encodes the mutant viral capsid, the reporter protein, and the drug-resistance protein, each of which can be on the same or different vector(s), operably linked to the same or different promoter(s).

Certain embodiments include libraries of at least one of the isolated cells or cell lines described herein. Included are cell libraries that comprise a plurality of isolated cells or cell lines described herein, wherein the non-naturally-occurring mutant viral capsid of each cell is distinct from the mutant viral capsid of substantially all of the other cells of the library. In some embodiments, the mutant viral capsid of each cell is distinct from the mutant viral capsid of about or at least about 90, 91, 92, 93, 94, 95, 96, 97, 98, 99, or 100% of the other cells of the library. Certain libraries include at least about 2, 5, 10, 20, 50, 100, 200, 300, 400, 500, 1000, 2000, 3000, 4000, 5000, 6000, 7000, 8000, 9000, 10000, 20000, 30000, 40000, 50000, 60000, 70000, 80000, 90000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ cells, wherein the mutant capsid of each cell is distinct from the mutant capsid of substantially all of the other cells of the library. In specific embodiments, the mutant viral capsid is a mutant AAV capsid.

In some embodiments, substantially all of the plurality of cells in the library have only one integration event of a polynucleotide that encodes a mutant viral capsid. In particular embodiments, about or at least about 90, 91, 92, 93, 94, 95, 96, 97, 98, 99, or 100% of the cells in the library have one integration event of a polynucleotide that encodes a mutant viral capsid. In specific embodiments, substantially all of the cells in the library contain a single integration event of a unique viral mutant capsid relative to the other cells in the library.

Also included are mixtures of at least two of the isolated cells or cell lines described herein, for example, mixtures of at least about 2-10,000 (including all integers and ranges in between, for example, 2, 5, 10, 20, 50, 100, 200, 300, 400, 500, 1000) of the isolated cells or cell lines described herein.

Certain embodiments include cell culture devices or plates, comprising an isolated cell or a mutant viral capsid cell library, as described herein. In some embodiments, each cell culture device or well therein comprises about or at least about 1, 2, 5, 10, 20, 50, 100, 200, 300, 400, 500, 1000, 2000, 3000, 4000, 5000, 6000, 7000, 8000, 9000, 10000, 20000, 30000, 40000, 50000, 60000, 70000, 80000, 90000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ or more cells. Included are cell culture devices, for example, multi-well plates (e.g., microplates) that comprise about or at least about 2, 6, 12, 24, 48, 96, 192, 384, 1536 or more wells. Also included are tissue culture dishes, flasks, T-flasks, roller bottles, cell factories, and suspension cultures, for example, in 1 L and 5 L spinners, 5 L, 14 L, 40 L, 100 L and 200 L stir tank bioreactors, and 20/50 L and 100/200 L WAVE bioreactors, among others known in the art.

Any of the libraries or cell culture devices/plates can be configured for high-throughput screening (HTS). The isolated cells or cell lines, including libraries and mixtures thereof, can be used in any of the methods, systems, or kits described herein.

Vector Systems for the Preparation of Mutant Capsids, Cells, and Cell Libraries

Certain embodiments include systems, for example, vector systems, for generating one or more cells that comprise a non-naturally-occurring mutant viral capsid, and libraries of such cells, that is, vector systems for the preparation of mutant viral capsid cell libraries.

Particular examples include a system for generating a mutant viral capsid cell library, comprising a system (e.g., vector system) for inserting a plasmid into a native (i.e., endogenous) DNA attachment site in the genome of a eukaryotic cell, comprising (a) a vector encoding a mutant viral capsid which is operably linked to a promoter and flanked by Inverted Terminal Repeats (ITRs), and comprising an integrase-specific DNA attachment site which recombines with the native DNA attachment site in the genome of the cell, and (b) a vector encoding an integrase which is operably linked to a promoter, wherein the integrase promotes integration of the vector of (a) into the native DNA attachment site in the genome of the cell.

These and related embodiments can be used to insert or integrate a plasmid encoding the mutant viral capsid into a native DNA attachment site in the genome of a cell of essentially any type, for example, a cell that has not been engineered to contain an integrase-specific DNA attachment site. In some instances, the vector of (a), which encodes the mutant viral capsid is titrated to minimize the occurrence of multiple integration events, and increase the probability that each transfected cell will contain only one integration event or copy of a mutant viral capsid. In specific embodiments, the mutant viral capsid is a mutant AAV capsid.

In certain embodiments, the integrase is a serine recombinase, for example, the phage integrase Bxb1, the phage integrase φC31, the phage integrase TP901-1, the phage integrase R4, the phage integrase φFC1, the resolvase Tn3, the resolvase γδ, or the invertase Gin. In some embodiments, the integrase is a tyrosine integrase, for example, lambda integrase, HK022 integrase, P22 integrase, HP1 integrase, L5 integrase, Cre recombinase, FLP invertase, and XerC.

In particular embodiments, the native DNA attachment site is a pseudo attP site. In some embodiments, the native DNA attachment site is a pseudo attP site, the integrase-specific attachment site in the vector of (a) is φC31 attB, and the integrase is φC31. In certain embodiments, the native DNA attachment site is a pseudo attP site, the integrase-specific attachment site in the vector of (a) is Bxb1 attB, and the integrase is Bxb1. Certain systems further comprise a plurality of eukaryotic cells (e.g., HEK-293 cells) in which the native DNA attachment site is in the genome of the cells. In some embodiments, the vector of (a) and (b) are on the same vector (e.g., the same plasmid). In some embodiments, the vector of (a) encodes a reporter protein, as described herein and known in the art. In some instances, the polynucleotide which encodes the reporter protein is located between the ITRs, that is, it is flanked by the ITRs. In certain embodiments, the vector of (a) encodes a drug resistance gene, as described herein and known in the art. In some instances, the polynucleotide encoding the drug resistance gene is located outside of the ITRs, that is, it is not flanked by the ITRs.

Also included are systems for generating a mutant viral capsid cell library, comprising (a) a system for introducing a first integrase-specific DNA attachment site into the genome of the eukaryotic cell, comprising (i) a vector comprising the first integrase-specific DNA attachment site and a second integrase-specific DNA attachment site (e.g., attB site) which recombines with a DNA attachment site in the genome of the cell (e.g., native pseudo attP site), and (ii) a vector encoding a first integrase which is operably linked to a promoter, wherein the first integrase promotes integration of the vector of (a)(i) into the genome of the cell via recombination between the second integrase-specific attachment site (e.g., attB site) and the DNA attachment site in the genome of the cell (e.g., native pseudo attP site); and (b) a system for inserting a plasmid into the first DNA attachment site in the genome of a eukaryotic cell, comprising (i) a vector encoding a mutant viral capsid which is operably linked to a promoter and flanked by Inverted Terminal Repeats (ITRs), and comprising a third integrase-specific DNA attachment site which recombines with the first integrase-specific DNA attachment site, and (ii) a vector encoding a second integrase which is operably linked to a promoter, wherein the second integrase promotes integration of the vector of (b)(i) into the first integrase-specific DNA attachment site.

These and related embodiments can be used initially to engineer a desired, integrase-specific DNA attachment site into the genome of essentially any cell (e.g., using a native pseudo attP site in the cell and an attB site in the vector of (a)(i)), and after that insert the vector encoding the mutant viral capsid (which has the corresponding attachment site) into the genome of the cell at the engineered DNA attachment site. In some instances, it will be useful to ensure that only a single copy of the first integrase-specific DNA attachment site is inserted into the genome of the cell, so that only one copy of the mutant viral capsid vector will be integrated into the genome of the cell. In specific embodiments, the mutant viral capsid is a mutant AAV capsid.

As noted above, illustrative examples of integrases or recombinases suitable for use in embodiments of the present disclosure include, but are not limited to, serine recombinases and tyrosine recombinases. Exemplary serine recombinases include the phage integrase Bxb1, the phage integrase φC31, the phage integrase TP901-1, the phage integrase R4, the phage integrase φFC1, the resolvase Tn3, the resolvase γδ, and the invertase Gin. Exemplary tyrosine recombinases include lambda integrase, HK022 integrase, P22 integrase, HP1 integrase, L5 integrase, Cre recombinase, FLP invertase, and XerC. In specific embodiments, the integrase is a Bxb1 integrase which promotes integration of DNA into a Bxb1 attB or Bxb1 attP DNA attachment site. In particular embodiments, the integrase is a φC31 integrase which promotes integration into a pseudo attP, φC31 attP, or φC31 attB DNA attachment site.

Examples of integrase-specific DNA attachment sites include, without limitation, attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product or hybrid DNA attachment sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, specific strategies position by homologous recombination an attP-bearing "docking site" into a defined locus, which is then partnered with an attB-bearing incoming sequence for insertion.

The native attB and attP recognition sites of phage φC31 (bacteriophage φC31) are generally about 34 to 40 nucleotides in length (see Groth et al., PNAS USA. 97:5995-6000, 2000). These sites are typically arranged as follows: AttB comprises a first DNA sequence attB5', a core region, and a second DNA sequence attB3', in the relative order from 5' to 3' attB5'-core region-attB3'. AttP comprises a first DNA sequence attP5', a core region, and a second DNA sequence attP3', in the relative order from 5' to 3' attP5'-core region-attP3'. The core region of attP and attB of φC31 has the sequence 5'-TTG-3'. Other phage integrases (such as the Bxb1 phage integrase) and their recognition sequences can be adapted for use according to the embodiments described herein. Exemplary phage integrase-specific DNA attachment sites are provided in Table A1 below.

TABLE A1

Phage Integrase-Specific DNA Attachment Sites

| Name | Sequence | |
|---|---|---|
| φC31 attP | GTCAGAAGCG GTTTTCGGGA GTAGTGCCCC AACTGGGGTA ACCTTTGAGT TCTCTCAGTT GGGGGCGTAG GGTCGCCGAC ATGACACAAG G | SEQ ID NO: 1 |
| φC31 attB | GACGGTCTCG AAGCCGCGGT GCGGGTGCCA GGGCGTGCCC TTGGGCTCCC CGGGCGCGTA CTCCACCTCA CCCATCTGGT CCATCATGAT | SEQ ID NO: 2 |
| Bxb1 attP | CGTGATGACC TGTGTCTTCG TGGTTTGTCT GGTCAACCAC CGCGGTCTCA GTGGTGTACG GTACAAACCC ATGAGAGCCC TGGTAGTCAT | SEQ ID NO: 3 |
| Bxb1 attB | CCGGCTTGTC GACGACGGCG GTCTCCGTCG TCAGGATCAT | SEQ ID NO: 4 |
| TP901-1 attP | AGATATCATA TTTAAATTCC AACTCGCTTA ATTGCGAGTT TTTATTTCGT TTATTTCAAT TAAGGTAACT AAAAAACTCC TTTTAAGGAG | SEQ ID NO: 5 |
| TP901-1 attB | TTAAAATACT GATAATTGCC AACACAATTA ACATCTCAAT CAAGGTAAAT GCTTTTTGCT TTTTTTGCCA AAGCTTTCTT CCGTGAATTT | SEQ ID NO: 6 |

Thus, the vectors, cells, and systems described herein can use any one or more of the foregoing phage native or integrase-specific DNA attachment sites, arranging the combinations as is appropriate (e.g., attP site recombines with an attB site). In specific embodiments, for the system of (a) above, the first integrase-specific DNA attachment site is Bxb1 attP, the second integrase-specific attachment site is φC31 attB, and the first integrase is φC31. In particular embodiments, for the system of (b) above, the third DNA attachment site is Bxb1 attB, and the second integrase is Bxb1.

For the tyrosine recombinases, one example of an integrase-specific DNA attachment site for Cre recombinase is loxP which is an approximately 34 base pair sequence comprising two 13 base pair inverted repeats (serving as the recombinase binding sites) flanking an 8 base pair core sequence (see, e.g., Sauer, Current Opinion in Biotechnology 5:521-527, 1994). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995). Suitable recombinase recognition sites for the FLP recombinase include, but are not limited to: FRT (McLeod, et al., 1996), F1, F2, F3 (Schlake and Bode, 1994), F4, F5 (Schlake and Bode, 1994), FRT(LE) (Senecoff et al., 1988), FRT(RE) (Senecoff et al., 1988). Thus, the vectors and systems described herein can use any one or more of the foregoing integrase-specific DNA attachment sites, arranging the combinations as is appropriate.

Certain systems comprise a plurality of eukaryotic cells, which comprise a native DNA attachment site in the genome of the cell that recombines with the second integrase-specific DNA attachment site. As noted herein, examples of native DNA attachment sites include pseudo attP sites.

In some systems, the vector of (a)(i) and (a)(ii) are on separate vectors. In particular instances, the vector of (b)(i) and (b)(ii) are on separate vectors. In some embodiments, the vector of (b)(i) encodes a reporter protein, as described herein and known in the art. In some instances, the polynucleotide which encodes the reporter protein is located between the ITRs, that is, it is flanked by the ITRs. In certain embodiments, the vector of (b)(i) encodes a drug resistance gene, as described herein and known in the art. In some instances, the polynucleotide encoding the drug resistance gene is located outside of the ITRs, that is, it is not flanked by the ITRs.

Any convenient vector that finds use delivering polynucleotide sequences to cells is encompassed by the systems and vectors of the present disclosure. For example, the vector may comprise single or double stranded nucleic acid, e.g. single stranded or double stranded DNA. For example, the gene delivery vector may be a naked DNA, e.g. a plasmid, a minicircle, etc. As another example, the vector may be a virus, e.g., an alphavirus, an adenovirus, an adeno-associated virus, a herpes virus, a retrovirus (e.g., M-MuLV, MoMSV, HaMuSV, MuMTV, GaLV, FLV, spumavirus, Friend murine leukemia virus, MSCV, and RSV) or a lentivirus (e.g., HIV including HIV type 1 and HIV type 2, VMV, CAEV, EIAV, FIV, BIV, and SIV)). While embodiments encompassing the use of adeno-associated virus are described in greater detail herein, it is expected that the ordinarily skilled artisan will appreciate that similar knowledge and skill in the art can be brought to bear on non-AAV vectors as well. See, for example, the discussion of retroviral vectors in, e.g., U.S. Pat. Nos. 7,585,676 and 8,900,858; the discussion of lentiviral vectors in, e.g., Naldini et al., (1996a, 1996b, and 1998); Zufferey et al., (1997); Dull et al., 1998, U.S. Pat. Nos. 6,013,516; and 5,994,136; and the discussion of adenoviral vectors in, e.g. U.S. Pat. No. 7,858,367, the full disclosures of which are incorporated herein by reference.

Certain embodiments include kits, which comprise any one or more of the systems (e.g., vector systems), isolated cells, cells, and/or cell libraries described herein. Some kits can optionally include instructions for using the systems to generate a mutant viral capsid cell library, as described herein. In specific embodiments, the mutant viral capsid cell library is a mutant AAV capsid cell library.

Methods of Preparing and Screening Mutant Capsid Cells and Cell Libraries

Certain embodiments relate to methods for generating a mutant viral capsid cell library, comprising (a) transfecting a plurality of eukaryotic cells with a first and a second vector, wherein the plurality of cells comprise an integrase-specific DNA attachment site in their genome, wherein the first vector encodes a mutant viral capsid which is operably linked to a promoter which is flanked by Inverted Terminal Repeats (ITRs) and comprises an integrase-specific DNA attachment site that recombines with the integrase-specific DNA attachment site in the cell, and wherein the second vector encodes a heterologous integrase which promotes integration at the DNA attachment site, and (b) selecting the plurality of cells for expression of the first vector, thereby generating the mutant viral capsid library. In specific embodiments, the mutant viral capsid is a mutant AAV capsid. These particular methods are useful, for example, for transfecting cells that contain the desired, integrase-specific DNA attachment site in the genome of the cells (e.g., a native pseudo attP site, or an engineered site), but which do not already express the corresponding integrase.

In particular embodiments, the integrase-specific DNA attachment site in the genome of the cells is a single non-native Bxb1 attP site, the integrase is Bxb1, and the integrase-specific DNA attachment site in the vector is Bxb1 attB. In certain embodiments, the integrase-specific DNA attachment site in the genome of the cells is a single non-native φC31 attP site, the integrase is φC31, and the integrase-specific DNA attachment site in the vector is φC31 attB. In some instances, substantially all of the selected cells have only one integration event of the vector which is at the single, non-native attP site. For example, in certain embodiments, about or at least about 90, 91, 92, 93, 94, 95, 96, 97, 98, 99, or 100% of the cells have only one integration event of the vector which is at the single non-native attB or attP site.

In some embodiments, the integrase-specific DNA attachment site in the genome of the cell is a native pseudo attP site, the integrase is Bxb1, and the integrase-specific DNA attachment site in the vector is Bxb1 attB. In particular embodiments, the integrase-specific DNA attachment site in the genome of the cell is a native pseudo attP site, the integrase is φC31, and the integrase-specific DNA attachment site in the vector is φC31 attB. In certain instances, substantially all of the selected cells have only one integration event of the vector at a pseudo native attP site. For example, in certain embodiments, about or at least about 90, 91, 92, 93, 94, 95, 96, 97, 98, 99, or 100% of the cells have only one integration event of the vector which is a pseudo native attP site. Certain of these and related methods include transfecting a titrated amount of the vector that encodes the mutant viral capsid to increase the probability that only one integration event will occur in substantially all of the selected cells. As one example, certain embodiments include the transfection of the first (mutant viral capsid) and second (integrase) vectors, where the ratio (e.g., molar ratio) of the first:second vectors can be about 1:50, 1:40, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, or 1:2, in specific instances about 1:10.

According to some embodiments, following transfection with first and second vectors, less than 10% and more preferably less than 5% of the cells comprise two or more vectors encoding a mutant viral capsid. The ratio of first:second vectors is titrated such that preferably less than 10%, and more preferably less than about 5% of the cells from step (a) undergo two or more integration events.

In some embodiments, the vector that encodes the mutant viral capsid further encodes a reporter protein, as described herein. In specific instances, the reporter protein is a green fluorescent protein (GFP).

In specific embodiments, the mutant viral capsid is a mutant AAV capsid. In these and related embodiments, certain methods comprise transfecting the mutant AAV capsid cell library with an AAV rep-expressing polynucleotide that encodes one or more of Rep78, Rep68, Rep52, and/or Rep40, and/or an AAV helper vector or plasmid, and incubating the cell library for a time sufficient to produce virions, e.g., AAV virions, which comprise the mutant capsid. Some methods comprise contacting the cells with a helper virus encoding a rep protein, and incubating the cell library for a time sufficient to produce virions that comprise the mutant AAV capsid. Exemplary helper viruses include adenovirus, retroviruses, and herpes virus.

Virions, e.g., AAV or other virions comprising a mutant capsid, can be produced using standard methodology. For example, in the case of AAV virions or AAV virus particles, an AAV helper construct may be introduced into the mutant viral capsid-containing cells or cell libraries, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient AAV virion production. The producer cells are then cultured to produce AAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

In the case of other virions, as noted above, the mutant viral capsid-containing cells or cell libraries may be contacted with a helper virus that comprises or encodes the necessary rep protein(s). Examples of such helper viruses include adenovirus and herpes virus. The virions, e.g., AAV virions, that comprise the mutant viral capsid can be collected and optionally purified and formulated according to techniques in the art (see, e.g., the Examples).

When generating a library of variant AAV virions for in vivo or in vitro screening, it is important to avoid, or at the very least minimize, the occurrence of cross packaging. An advantage of the present invention is the prevention or minimization of cross packaging. Cross packaging occurs when the polynucleotide sequence encoding one mutant is packaged by the capsid proteins of another mutant. Cross packaging makes it difficult if not impossible to trace the properties of the capsid (e.g., tropism, antibody reactivity, heparan sulfate binding, etc.) to the sequence encoding the capsid, resulting both in the identification of a false-positive mutant capsid (that does not embody the preferred tropism properties) and the loss of the actual mCap cDNA encoding the mutant capsid with the preferred tropism properties.

Without wishing to be bound by any theory, it is believed that the probability that the genome of one variant will be packaged or encapsidated by the capsid proteins of a different AAV genome increases with the number of capsid genes per cell. When multiple variant AAV genomes are present in the same cell, the translation and replication of each genome may give rise to a complex mixture of viral DNA, VP1, VP2, and VP3 capsid proteins. Under these conditions, AAV genomes may be incorrectly encapsidated by the capsid proteins of another genome and capsid proteins derived from two or possibly even three different genomes may assemble to form hybrid capsids that, ultimately, cannot be linked to any particular genome or group of genes. For these reasons, it was important to develop a method that favors a single integration event of just one capsid gene per cell.

Certain embodiments include screening the virions, e.g., AAV virions, for at least one phenotype. In some embodiments, the virions are screened for at least one phenotype relative to a corresponding, wild-type AAV capsid, for example, a virion that comprises a corresponding, wild-type AAV capsid. Typically, the at least one phenotype will relate to the properties of the AAV capsid, including, for example, altered cell tropism, reduced neutralizing antibody binding, or both.

Certain embodiments include screening mutant viral capsids for altered cell tropism, for instance, by screening the virions produced by a mutant viral capsid cell library for the ability to infect a given target cell, and thereby identifying a mutant viral capsid of interest. For example, see FIG. 1B. Thus, certain embodiments include screening the virions (e.g., w/mutant AAV capsids) for altered cell tropism, for example, relative to virion that comprises a corresponding, wild-type AAV capsid. In certain embodiments, a mutant viral capsid of interest has increased cell tropism towards a target cell, for example, relative to a corresponding wild-type capsid (e.g., AAV). In some embodiments, a mutant viral capsid of interest has reduced cell tropism towards a target cell, relative to a corresponding wild-type capsid (e.g., AAV). These and related embodiments include infecting target cells with the virions (e.g., w/mutant AAV capsids) under suitable conditions. In some instances, the virions comprise a reporter gene (or encode a reporter gene), and the methods optionally include isolating infected cells based on expression of the reporter protein. For fluorescent reporter proteins such as GFP, infected cells can be isolated according to any variety of techniques, including cell sorting by FACS (Fluorescence-activated cell sorting) or flow cytometry. In some instances, infected cells can be isolated without cell sorting, for example, by processing the population of infected cells (in whole or in part) directly from tissue culture or by excising and processing a tissue of choice (e.g., for screens/infections performed in vivo). In these and related embodiments, assays such as RT-PCR can be performed to identify the mutant capsids of interest.

Exemplary target cells for screening for altered cell tropism include ocular cells such as photoreceptor cells (cone cells, rod cells), retinal pigment epithelium cells, bipolar cells, ganglion cells, horizontal cells, amacrine cells, Muller glial cells and corneal epithelial cells, lung cells (e.g., alveolar type I epithelial cells or pneumocytes, alveolar type II cells or pneumocytes, capillary endothelial cells, alveolar macrophages) liver cells (e.g., hepatocytes, sinusoidal endothelial cells, phagocytic Kupffer cells, hepatic stellate cells, intrahepatic lymphocytes), cardiac cells (e.g., atrial and ventricular cardiomyocytes, cardiac fibroblasts, endothelial cells, cardiac smooth muscle cells, cardiac pacemaker cells, Purkinje fibers), brain cells, peripheral nerve cells (neurons, Schwann cells), central nervous system and brain cells (neurons, glial cells including astrocytes, oligodendrocytes, and microglia), cells of the musculoskeletal system (e.g., myocytes, smooth muscle cells, chondrocytes, osteoclasts, osteoblasts), cells of the gastrointestinal system (e.g., enterocytes, Goblet cells, enteroendocrine cells, Paneth cells), pancreatic cells (e.g., α alpha cells, β beta cells, δ delta cells, γ (gamma) cells), skin cells (e.g., keratinocytes, melanocytes, Merkel cells, Langerhans cells). Additional examples of target cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including Th1 and Th2 cells), natural killer cells, γδ T-cells, dendritic cells, and mast cells. Examples of vascular cells include smooth muscle cells, endothelial cells, and fibroblasts. In specific embodiments, the target cells are retinal cells, and the altered cell tropism comprises increased cell tropism to or infectivity of retinal cells.

In some embodiments, the at least one phenotype is reduced neutralizing antibody binding (see, e.g., Rapti et al., Molecular Ther. 20:73-83, 2010; and Calcedoa et al., The Journal of Infectious Diseases. 199:381-390, 2009). In this regard, the presence of neutralizing antibodies to AAV as a result of previous exposure can significantly limit effective gene transfer using AAV vectors. Certain embodiments therefore include screening mutant viral capsids for reduced neutralizing antibody binding, for instance, by testing the vector particles produced by a mutant viral capsid library for the ability to infect a given target cell in the presence of neutralizing antibodies. Certain of these and related embodiments include infecting target cells with the virions (e.g., w/mutant AAV capsids) in the presence of neutralizing antibodies (e.g., sera from subjects previously exposed to AAV), and identifying a mutant viral capsid of interest. In certain embodiments, the virion(s) comprising the mutant viral capsid of interest show infectivity towards the target cell in the presence of neutralizing antibodies. In certain embodiments, the virion(s) comprising the mutant viral capsid of interest show increased infectivity towards the target cell in the presence of neutralizing antibodies, relative to a corresponding wild-type capsid (e.g., AAV capsid). In particular embodiments, the increased infectivity is statistically significant, as described herein and known in the art.

Certain methods include performing reverse transcription polymerase chain reaction (RT-PCR) on RNA from the infected, isolated cells or virions (e.g., w/mutant AAV capsids) to identify and sequence a mutant AAV capsid of interest. This approach can provide advantages relative to the sequence of genomic DNA, because the latter can sometimes contain, for example, non-expressed or inactive capsid sequences that differ from the active capsid sequence of interest, and which can confound efforts to identify and confirm the sequence of the mutant capsid of interest.

For example, in relation to studies intended to screen for mutant AAV virions that might have applications for treatment of retinal diseases, it may be desirable to identify a viral vector that can deliver a therapeutic gene to the back of the eye upon administration to the vitreous body in the front of the eye. However, while some AAV particles may cross from the vitreous to the retina, they may not infect or transduce retinal cells. When extracting retinal cell tissue for analysis, these non-infectious AAV particles can contaminate the PCR sample and may contribute to the signal that is attributed to infectious particles. The present method and system uses RT-PCR to specifically amplify AAV mRNA only, which detects only those genomes that have successfully infected cells and avoids false-positive signals due to AAV DNA carried by non-infectious virions located in the extracellular matrix or on the cell surface only.

Also included are steps for increasing the quantity of mutant AAV capsid RNA in an infected target cell. Such steps can be performed prior to and in addition to RT-PCR. In some instances, increasing the quantity of mutant AAV capsid RNA in an infected target cell comprises transducing isolated target cells with an adenovirus or a herpes simplex virus (e.g., HSV-1) prior to performing RT-PCR. In some embodiments the adenovirus is Ad5. Such procedures for transducing cells or tissues with an adenovirus or HSV-1 can, for example, be performed on target cells and tissues after removing the target cells or tissue from the mammalian subject to which a mutant AAV virion library was administered. The transduction step can then be followed by the step of performing RT-PCR on RNA from the target cells or tissue.

Accordingly, the present invention further includes pharmaceutical compositions comprising a plurality of mutant virions of this disclosure, or more specifically mutant AAV virions, and a pharmaceutically acceptable carrier. Non-limiting examples of such carriers include water, physiological saline, and phosphate buffered saline (PBS). In some cases, the carrier is sterile and is fluid to the extent that easy syringability exists. By "pharmaceutically acceptable carrier" is meant a material that may be administered to a subject with little or no harmful effects.

Non-limiting illustrative examples of a mammalian subject include a non-human primate (e.g., a monkey), horse, pig, dog, mouse, rabbit, gerbil, or rat.

The mutant virions may be administered to the subject using any suitable means. The route of administration may depend on the target cells or tissue of interest. For example, mutant virions may be administered systemically. Specific routes of administration may include, but are not limited to, intravenous, intra-arterial, intramuscular, intraperitoneal, retro-orbital, intraocular, intravitreal, or sub-retinal administration. Other routes may comprise administration to the central nervous system. Among the many variations contemplated, a library of mutant virions, such as a library of mutant AAV virions, may be administered as a single dose or in separate pharmaceutical compositions simultaneously or sequentially.

The dosage of a mutant viral library administered to a test animal or mammalian subject for screening purposes may vary and may depend on a number of factors, such as route or mode of administration and body weight. For example, for delivery to large organs (e.g., liver, muscle, heart and lung) a preferred dosage may be about $5 \times 10^{10}$ to $1 \times 10^{13}$ AAV genomes per 1 kg of body weight. For delivery to the eye, it may be desirable to administer from about $1 \times 10^9$ to $5 \times 10^{12}$ vector genomes. Adjustments in dosage may be necessary to guard against possible side effects. In some embodiments, a sample of the variant viral library may be in a volume of about 0.1 mL to about 100 mL of solution containing from about $1 \times 10^9$ to $1 \times 10^{16}$ genomes virus vector.

In certain instances, the methods provided herein can include additional rounds of selection and screening. For example, a mutant viral capsid that is identified during one round of selection and screening as having one or more desirable properties (e.g., altered tropism, reduced neutralizing antibody binding) can be subject to another round of mutagenesis to generate a library of polynucleotides and cells that comprise additional viral capsid mutants. These can then be screened for the desired phenotypes. Such can be repeated, for example, one, two, three or more times, until the desired mutant viral capsid is obtained.

Accordingly, additional embodiments include compositions comprising an isolated mutant virus, or viral variant, or plurality of isolated viral variants, and a suitable diluent or carrier, wherein the viral variant or plurality of viral variants comprise(s) a capsid(s) having one or more amino acid substitutions, insertions, or deletions relative to a corresponding parental viral capsid, and wherein the viral variant or plurality of viral variants has/have been produced from a cell library and identified and isolated by any one of the screening methods described herein. In some aspects, the viral variant is an AAV variant, and the plurality of viral variants are AAV variants. Suitable diluents include sterile, buffered, isotonic, aqueous liquids, or gels, solids, or semi-solids that preserve the activity of the virus and that can be administered to cells, tissues, or a mammalian subject with little or no toxicity.

Another embodiment is a mutant AAV virion or capsid identified by any of the methods described herein. Such methods can, for example, comprise the step of performing RT-PCR on RNA from an infected cell or target tissue to identify and sequence a mutant AAV capsid of interest, and may optionally further include the step of transducing the infected cell or target tissue with an adenovirus. According to one embodiment, transducing the infected cell or target tissue with an adenovirus is performed before performing RT-PCR.

Additionally, a cell library of the present invention allows for scalable production of a plurality of AAV virions having one or more mutations in their capsid protein. Because the coding sequence encoding the mutant capsid is stably integrated into the cellular genome and is not merely transiently transfected, a cell library of this disclosure can in theory be expanded by growth and passaging in culture to increase the number of cells, and therefore the number of mutant virus-encoding units in the library. The scalability of the present methods is expected to be of practical benefit for some directed evolution protocols, particularly those involving systemic administration, which may require significant quantities of virus to effectively identify mutant virions with a tropism toward large organs (e.g., heart, liver, lungs, kidney and the like).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

Example 1

Generating a Packaging Cell Library

Figure 1B:
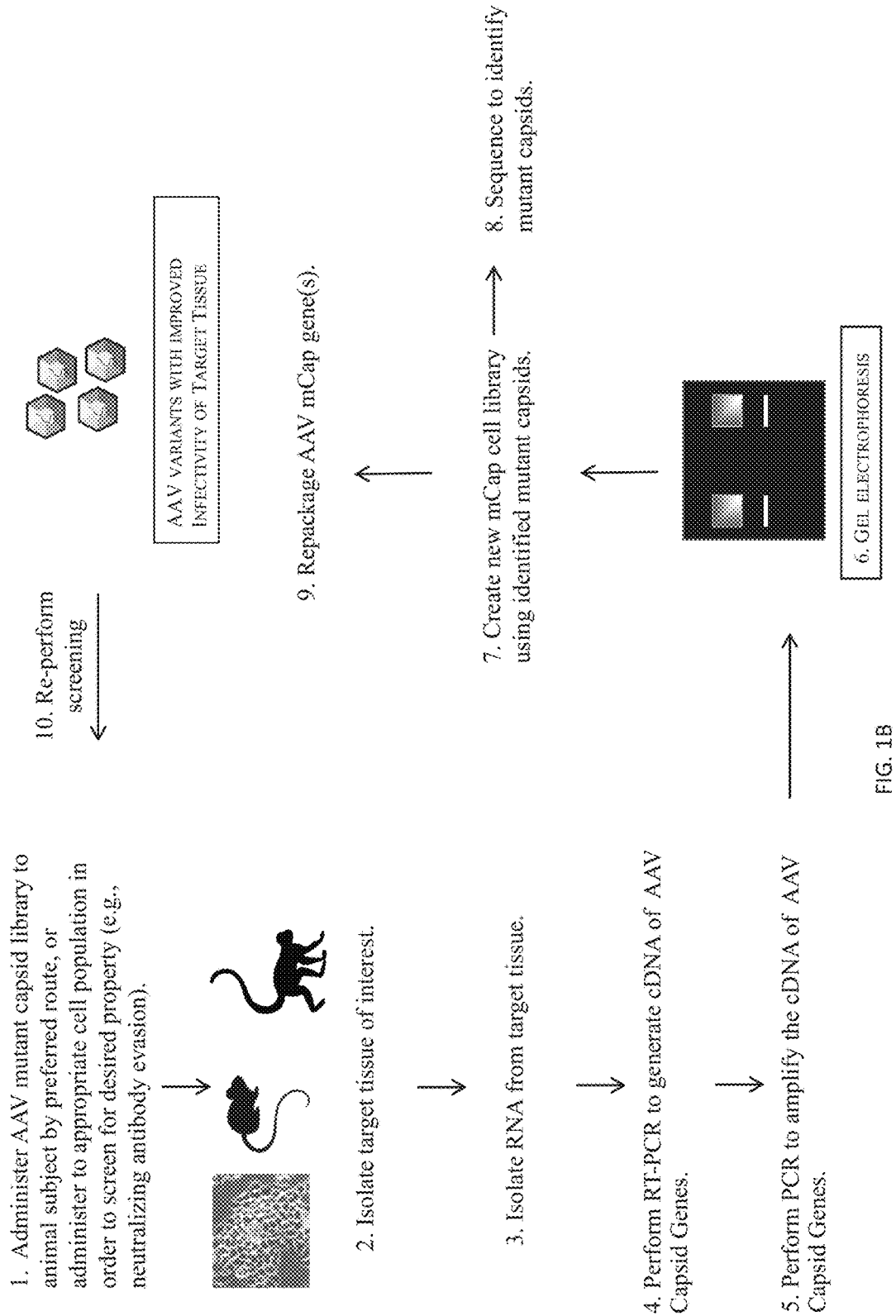

A packaging cell library was generated using a two-plasmid transfection approach. One plasmid encoded φC31 integrase and the other contained an attB attachment site and a polynucleotide expression cassette encoding the mutant AAV capsid (mCap) to be integrated (FIG. 1A). Phage integrase, φC31, is believed to be well tolerated by mammalian cells and integrates specifically at pseudo attP sites naturally present in the cellular genome (Calos, MP (2006) "The φC31 Integrase System for Gene Therapy" *Curr. Gene Ther.* 6(6):633-645; Chalberg et al. (2005) "φC31 Integrase Confers Genomic Integration and Long-Term Transgene Expression in Rat Retina" Investigative Ophthalmology & Visual Science 46 (6):2140-2146). In the plasmid containing the mCap cDNA, the mCap cDNA was operably linked to a CMV promoter and the expression cassette was flanked by ITRs. The cassette also contained a sequence encoding green fluorescent protein (GFP) operably linked to a separate promoter (e.g., SV40) to help identify and sort transfected and infected cells in later steps.

To generate a mutant AAV capsid cell library, HEK-293 (293) cells were split and seeded the day before transfection and incubated at 37° C. in a $CO_2$ incubator. Co-transfection was performed with a first plasmid that encoded the φC31 integrase and a second plasmid that encoded mutagenized AAV capsid cDNA linked to a strong CMV promoter and a GFP transgene linked to the SV40 promoter. The latter cassette was flanked between two AAV ITRs, and the backbone of the cassette contained an attB site for recombination and integration of the plasmid into pseudo attP sites in the cell genome. Also included was a neomycin resistance gene to allow for drug selection of cells expressing the second plasmid.

The co-transfection was performed at an approximately 50:1 ratio of the φC31 plasmid and the mutant AAV capsid plasmid. LIPOFECTAMINE® 3000 reagent was used to transfect the HEK293 cells.

After adding the transfection mix, cells were incubated for 24 hours and then split onto new plates and incubated at 37° C. in the $CO_2$ incubator for an additional 24 hours. The cells were then placed under G418 selection for 2 weeks. After colony formation, the cells were trypsinized, and pooled. This is the cell library.

To generate virions for screening, the cell library was plated such that the cells are at 85-90% confluency after 3 days. On day 3 after plating, the cell library was co-transfected with Ad-helper plasmid and Rep2-expressing plasmid. After about five days, the cells were harvested and lysed to isolate the virions that comprise the viral mutant capsids, which were purified by iodiaxonal gradient, formulated, and then used for screening.

Example 2

Controlling Integration Frequency

When generating a library of variant AAV virions for in vivo or in vitro screening, it is important to avoid, or at the very least minimize, the occurrence of cross packaging. Cross packaging occurs when the polynucleotide sequence encoding one mutant is packaged by the capsid proteins of another mutant. Cross packaging makes it difficult if not impossible to trace the properties of the capsid (e.g., tropism, antibody reactivity, heparin sulfate binding, etc.) to the sequence encoding the capsid, resulting both in the identification of a false-positive mutant capsid (that does not embody the preferred tropism properties) and the loss of the actual mCap cDNA encoding the mutant capsid with the preferred tropism properties.

For these reasons, it was important to develop a method that favors a single integration event of just one capsid gene per cell. We investigated how integration frequency may depend on the ratio of integrase-encoding plasmid to mutant capsid-encoding plasmid carrying the attB site. Cells were transfected with first and second donor plasmids together with a third plasmid encoding φC31 integrase. The first donor plasmid contained an expression cassette encoding red fluorescent protein (RFP), while the second donor plasmid contained an expression cassette encoding green fluorescent protein (GFP). Each of the donor plasmids contained an attB DNA attachment site for integration into the genome and a neomycin resistance gene for drug selection.

HEK 293 cells were transfected with a mixture of first, second, and third plasmids at a donor plasmid (equal parts RFP and GFP plasmids) to integrase-encoding plasmid ratio of 1:1, 1:10, 1:50, 1:100, and 1:200, using FuGENE® 6 transfection reagent. After selection with G418, "red" (cells containing RFP) and "green" (cells containing GFP) colonies were counted along with colonies expressing both RFP and GFP. Colonies that emitted red only or green only were counted as single integrants, and colonies that emitted both red and green fluorescence were counted as double integrants. The percentage of red-only and green-only colonies that might possibly have contained some cells having two or more copies of the RFP or GFP gene, respectively, was estimated to be roughly equivalent to the percentage of colonies exhibiting both red and green fluorescence and was accounted for as part of the analysis.

Figure 2:
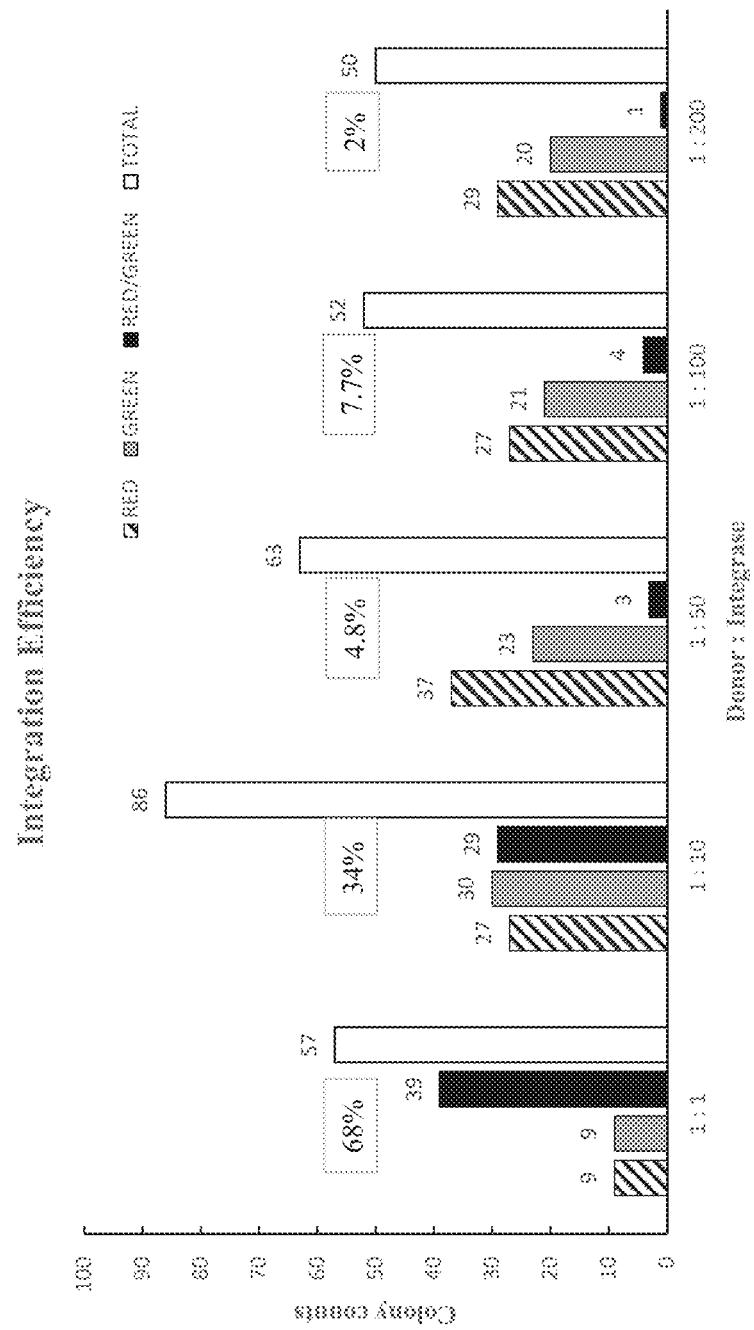
FIG. 2 shows how integration frequency or rate (number of integration events per cell) depends on the molar ratio of donor plasmid (attB-containing and mutant viral capsid-encoding plasmid) to φC31 integrase-encoding plasmid. Numbers above each bar show the number of cells counted that incorporated only the sequence encoding the red reporter (cross-hatched bars), the number of cells that incorporated only the sequence encoding the green reporter (light gray bars), and the number of cells that incorporated both red and green coding sequences (i.e., double integrants; solid bars). Also shown is the total number of cells counted in each study (non-filled bars). The percentage of double integrant cells (i.e., % cells in which two or more integration events occurred) is shown for each molar ratio tested.

As shown in FIG. 2, the number of double integrants, expressed as a percentage of the total number of colonies counted, generally decreased as the amount of donor plasmid relative to integrase-encoding plasmid was decreased from a donor:integrase plasmid ratio of 1:1 to 1:200. A 1:50 ratio of donor to integrase plasmid was deemed optimal because it maintained the highest amount of donor plasmid integration, which can be an important factor for achieving high diversity during the generation of a mutant viral capsid library, and because it resulted in a low (less than about 10%) double integration rate.

Example 3

Screening AAV Variants In Vivo

It was of interest to ascertain whether we are able to identify virions with altered tropism and/or other beneficial properties from performing a screen using a library of mutant AAV virions produced in accordance with this disclosure. Without limitation, a mutant AAV virion may, for example, exhibit one or more of the following properties: 1) increased heparan sulfate binding affinity relative to wild-type AAV; 2) decreased heparan sulfate binding affinity relative to wild-type AAV; 3) increased infectivity of a cell that is resistant to infection with AAV, or that is less permissive to infection with AAV than a prototypical permissive cell; 4) increased evasion of neutralizing antibodies; 5) increased ability to cross an endothelial cell layer (see, for example, U.S. Pat. No. 9,233,131); and 6) increased ability to cross the inner limiting membrane (ILM).

To further investigate the properties of one mutant AAV capsid library, a library of variant AAV virions was screened in vivo for the ability to pass through the inner limiting membrane (ILM) and infect retinal cells in non-human primate eyes. Generally, naturally occurring serotypes of AAV cannot effectively transduce photoreceptor cells in the back of the eye when the viruses are administered via intravitreal injection in the eye because they are unable to cross through the inner limiting membrane (ILM) (Dalkara et al. (2013) "In Vivo—Directed Evolution of a New Adeno- Associated Virus for Therapeutic Outer Retinal Gene Delivery from the Vitreous" Sci. Transl. Med. 5: 189ra76).

A sample of a mutant AAV capsid library produced according to the method generally depicted in FIG. 1A and containing mutant AAV virions with a random peptide insertion in a surface exposed region of the capsid, was injected intravitreally into the eyes of African Green monkeys. Six weeks post injection, the animals were sacrificed and retinal tissue explants from each animal were isolated and separately transduced with Ad5 virus (MOI of 1000). The Ad5 virus increases production of mutant AAV RNA that encodes for mCap in those target cells that were infected in the animal with the mutant AAV, thereby increasing the quantity of mutant capsid RNA in infected cells for subsequent detection by RT-PCR. After transduction with Ad5 and further incubation, retinal tissue punches were collected from each explant. RNA was then extracted from each of the tissue punches and converted to cDNA by RT-PCR followed by one round of PCR. These products were then cloned back into plasmids and sequenced to determine the sequences of mutant AAV capsids that were able to successfully cross the ILM and infect retinal cells in the monkey eye.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for generating a mutant adeno-associated virus (AAV) capsid cell library, comprising,
   (a) transfecting a plurality of eukaryotic cells with a first vector and a second vector, wherein the plurality of cells comprise an integrase-specific DNA attachment site in their genome, wherein the first vector comprises a polynucleotide sequence that encodes a mutant viral capsid operably linked to a promoter and comprises an integrase-specific DNA attachment site that recombines with the integrase-specific DNA attachment site in the cell, and wherein the second vector encodes a heterologous integrase which promotes integration at the DNA attachment site, and
   (b) selecting the plurality of cells for expression of the first vector, thereby generating the mutant viral capsid cell library, wherein less than 10% of the cells transfected in step (a) comprise two or more vectors encoding a mutant AAV capsid, wherein substantially all of the selected cells comprise a single heterologous polynucleotide encoding the mutant viral capsid integrated into the genome of the cell, and wherein the mutant viral capsid cell library encodes a plurality of mutant viral capsids.

2. The method of claim 1, wherein the integrase-specific DNA attachment site in the genome of the cell is a native pseudo attP site, the integrase is φC31, and the integrase-specific DNA attachment site in the first vector is φC31 attB.

3. The method of claim 2, comprising transfecting a titrated molar ratio of the first vector:second vector, wherein substantially all of the selected cells have only one integration event of the first vector at a pseudo native attP site.

4. The method of claim 1, further comprising transfecting the mutant AAV capsid cell library with an AAV rep-expressing polynucleotide that encodes one or more of Rep78, Rep68, Rep52, and/or Rep40, and/or a helper vector or plasmid, and incubating the cell library for a time sufficient to produce virions that comprise a mutant AAV capsid.

5. The method of claim 4, further comprising collecting and screening the virions for at least one phenotype, wherein screening comprises infecting target cells with the virions under suitable conditions or administering the virions to a mammalian subject, followed by isolating the infected target cells or isolating a target tissue from the mammalian subject.

6. The method of claim 5, further comprising performing reverse transcription polymerase chain reaction (RT-PCR) on RNA from the infected, isolated cells or tissue to identify and sequence a mutant AAV capsid of interest.

7. The method of claim 1, wherein the integrase-specific DNA attachment site in the genome of the cells is a single pseudo Bxb1 attP site, the integrase is Bxb1, and the integrase-specific DNA attachment site in the vector is Bxb1 attB.

8. The method of claim 1, wherein the integrase-specific DNA attachment site in the genome of the cells is a single pseudo φC31 attP site, the integrase is φC31, and the integrase-specific DNA attachment site in the vector is φC31 attB.

9. The method of claim 8, wherein substantially all of the selected cells have only one integration event of the vector which is at the single pseudo φC31 attP site.

10. The method of claim 1, wherein the vector that encodes the mutant viral capsid further encodes a reporter protein, optionally green fluorescent protein (GFP).

11. The method of claim 3, further comprising contacting the cells with a helper virus encoding a rep protein, and incubating the cell library for a time sufficient to produce virions that comprise a mutant AAV capsid.

12. The method of claim 11, wherein the helper virus is an adenovirus or a herpes virus.

13. The method of claim 12, comprising collecting and screening the virions for at least one phenotype relative to a wild-type AAV capsid, wherein the at least one phenotype is altered cell tropism, reduced neutralizing antibody binding, or both.

14. The method of claim 13, wherein screening comprises infecting target cells with the virions under suitable conditions and isolating the infected cells.

15. The method of claim 14, wherein isolating the cells or tissue is based on expression of a reporter protein encoded by the virions, wherein the reporter protein is optionally green fluorescent protein (GFP).

16. The method of claim 14, wherein the target cells comprise retinal cells and the at least one phenotype is increased tropism towards (or infectivity of) the retinal cells.

17. The method of claim 14, wherein the at least one phenotype is reduced neutralizing antibody binding and the suitable conditions comprise the presence of neutralizing antibodies.

18. The method of claim 17, wherein the target cells are HeRC32 cells which express a rep protein.

19. The method of claim 6, wherein prior to performing RT-PCR the method comprises increasing the quantity of mutant AAV capsid RNA in an infected target cell, which comprises the step of transducing the target cells or target tissue with an adenovirus or herpes simplex virus.

20. The method of claim 1, wherein the plurality of eukaryotic cells are transfected with the first vector and the second vector at a vector ratio of the first vector to the second vector of about 1:50.

\* \* \* \* \*

SEQUENCE LISTING

```
<160> NUMBER OF SEQ ID NOS: 6

<210> SEQ ID NO 1
<211> LENGTH: 91
<212> TYPE: DNA
<213> ORGANISM: Streptomyces phage phiC31

<400> SEQUENCE: 1
gtcagaagcg gttttcggga gtagtgcccc aactggggta acctttgagt tctctcagtt      60
gggggcgtag ggtcgccgac atgacacaag g                                    91

<210> SEQ ID NO 2
<211> LENGTH: 90
<212> TYPE: DNA
<213> ORGANISM: Streptomyces sp.

<400> SEQUENCE: 2
gacggtctcg aagccgcggt gcgggtgcca gggcgtgccc ttgggctccc cgggcgcgta      60
ctccacctca cccatctggt ccatcatgat                                      90

<210> SEQ ID NO 3
<211> LENGTH: 90
<212> TYPE: DNA
<213> ORGANISM: Mycobacterium phage Bxb1

<400> SEQUENCE: 3
cgtgatgacc tgtgtcttcg tggtttgtct ggtcaaccac cgcggtctca gtggtgtacg      60
gtacaaaccc atgagagccc tggtagtcat                                      90

<210> SEQ ID NO 4
<211> LENGTH: 40
<212> TYPE: DNA
<213> ORGANISM: Mycobacterium sp.
```

```
<400> SEQUENCE: 4
ccggcttgtc gacgacggcg gtctccgtcg tcaggatcat                40

<210> SEQ ID NO 5
<211> LENGTH: 90
<212> TYPE: DNA
<213> ORGANISM: Lactococcus phage TP901-1

<400> SEQUENCE: 5
agatatcata tttaaattcc aactcgctta attgcgagtt tttatttcgt ttatttcaat    60
taaggtaact aaaaaactcc ttttaaggag                                      90

<210> SEQ ID NO 6
<211> LENGTH: 90
<212> TYPE: DNA
<213> ORGANISM: Lactococcus sp.

<400> SEQUENCE: 6
ttaaaatact gataattgcc aacacaatta acatctcaat caaggtaaat gcttttttgct   60 tttttttgcca aagctttctt ccgtgaattt                                    90
```